US012078642B2

(12) United States Patent
Boon et al.

(10) Patent No.: US 12,078,642 B2
(45) Date of Patent: Sep. 3, 2024

(54) METHODS FOR EVALUATING AND IMPROVING COGNITIVE FUNCTION

(71) Applicants: THE UNIVERSITY OF MELBOURNE, Parkville (AU); THE FLOREY INSTITUTE OF NEUROSCIENCE AND MENTAL HEALTH, Parkville (AU)

(72) Inventors: Wah Chin Boon, North Melbourne (AU); Ute Roessner, Essendon (AU); Thusitha Wasantha Thilaka Pasinghe, Bundoora (AU); Enie Lei, Burwood East (AU)

(73) Assignees: THE UNIVERSITY OF MELBOURNE, Parkville (AU); THE FLOREY INSTITUTE OF NEUROSCIENCE AND MENTAL HEALTH, Parkville (AU)

( * ) Notice: Subject to any disclaimer, the term of this patent is extended or adjusted under 35 U.S.C. 154(b) by 453 days.

(21) Appl. No.: 16/762,794

(22) PCT Filed: Nov. 9, 2018

(86) PCT No.: PCT/AU2018/051207
§ 371 (c)(1),
(2) Date: May 8, 2020

(87) PCT Pub. No.: WO2019/090393
PCT Pub. Date: May 16, 2019

(65) Prior Publication Data
US 2020/0348318 A1 Nov. 5, 2020

(30) Foreign Application Priority Data
Nov. 9, 2017 (AU) .................................. 2017904551

(51) Int. Cl.
*G01N 33/68* (2006.01)
*A61K 31/575* (2006.01)
*G01N 33/50* (2006.01)
*G01N 33/92* (2006.01)

(52) U.S. Cl.
CPC ....... *G01N 33/6896* (2013.01); *A61K 31/575* (2013.01); *G01N 33/5088* (2013.01); *G01N 33/92* (2013.01); *G01N 2800/2821* (2013.01)

(58) Field of Classification Search
CPC ... A61K 31/575; A61P 25/28; G01N 33/6896; G01N 33/5088; G01N 33/92; G01N 2800/2821
See application file for complete search history.

(56) References Cited

U.S. PATENT DOCUMENTS

| 5,270,041 A | 12/1993 | Eugster |
| 2004/0115135 A1 | 6/2004 | Quay |
| 2007/0185035 A1 | 8/2007 | Constantino |
| 2010/0047163 A1* | 2/2010 | Forte ................ A61P 35/00 424/1.29 |
| 2012/0283323 A1 | 11/2012 | Silva et al. |
| 2017/0210775 A1 | 7/2017 | Ahmad et al. |

FOREIGN PATENT DOCUMENTS

JP  2010-083879 A  4/2010

OTHER PUBLICATIONS

Meng, Fanfei, et al., "A novel LDL-mimic nanocarrier for the targeted delivery of curcumin into the brain to treat Alzheimer's disease", *Colloids and Surfaces B: Biointerfaces*, Elsevier Amsterdam, NL, vol. 134, Jun. 19, 2015 (Jun. 19, 2015), pp. 88-97.
Nelson, Peter T. et al., "Correlation of Alzheimer Disease Neuropathologic Changes With Cognitive Status: A Review of the Literature", *Journal of Neuropathology and Experimental Neurology*, vol. 71, No. 5, May 1, 2012 (May 1, 2012), pp. 362-381.
Proitsi, P., et al., "Plasma lipidomic analysis finds long chain cholesteryl esters to be associated with Alzheimer's disease", *Translational Psychiatry*, vol. 5, No. 1, Jan. 1, 2015 (Jan. 1, 2015), pp. 1-8.
Proitsi, Petroula, et al., "Association of blood lipids with Alzheimer's disease: A comprehensive lipidomics analysis", *Alzheimer's & Dementia: The Journal of the Alzheimer's Association*, Elsevier, New York, NY, US, vol. 13, No. 2, Sep. 28, 2016 (Sep. 28, 2016), pp. 140-151.
Tully, A.M., et al., "Low serum cholesteryl ester-docosahexaenoic acid levels in Alzheimer's disease: a case-control study", *British Journal of Nutrition*, vol. 89, No. 4, Apr. 1, 2003 (Apr. 1, 2003), pp. 483-489.
European Patent Application No. 18875463.4, Extended European Search Report dated Oct. 29, 2021, 13 pages.
International Search Report received for PCT/AU2018/051207, dated Jan. 9, 2019.
Gowler, A.J. and Lamberty, Y., "The aged mouse as a model of cognitive decline with special emphasis on studies in NMRI mice." Behav Brain Res. 57(2):163-173 (1993) (Abstract).
Peters, O., et al., "Astrocyte Function is Modified by Alzheimer's Disease-like Pathology in Aged Mice." J Alzheimers Dis. 18(1): 177-189 (2009) (Abstract).

(Continued)

*Primary Examiner* — Olga N Chernyshev
(74) *Attorney, Agent, or Firm* — Kilpatrick Townsend & Stockton LLP

(57) ABSTRACT

The present invention generally relates to method for evaluating and improving cognitive function in a subject. In particular, the invention generally relates to methods for evaluating cognitive function in a subject by determining the level of cholesteryl esters in a subject, and to improving cognitive function in a subject comprising the administration of cholesteryl oleate, or analogues thereof.

4 Claims, 14 Drawing Sheets

(56) References Cited

OTHER PUBLICATIONS

Figure 1:
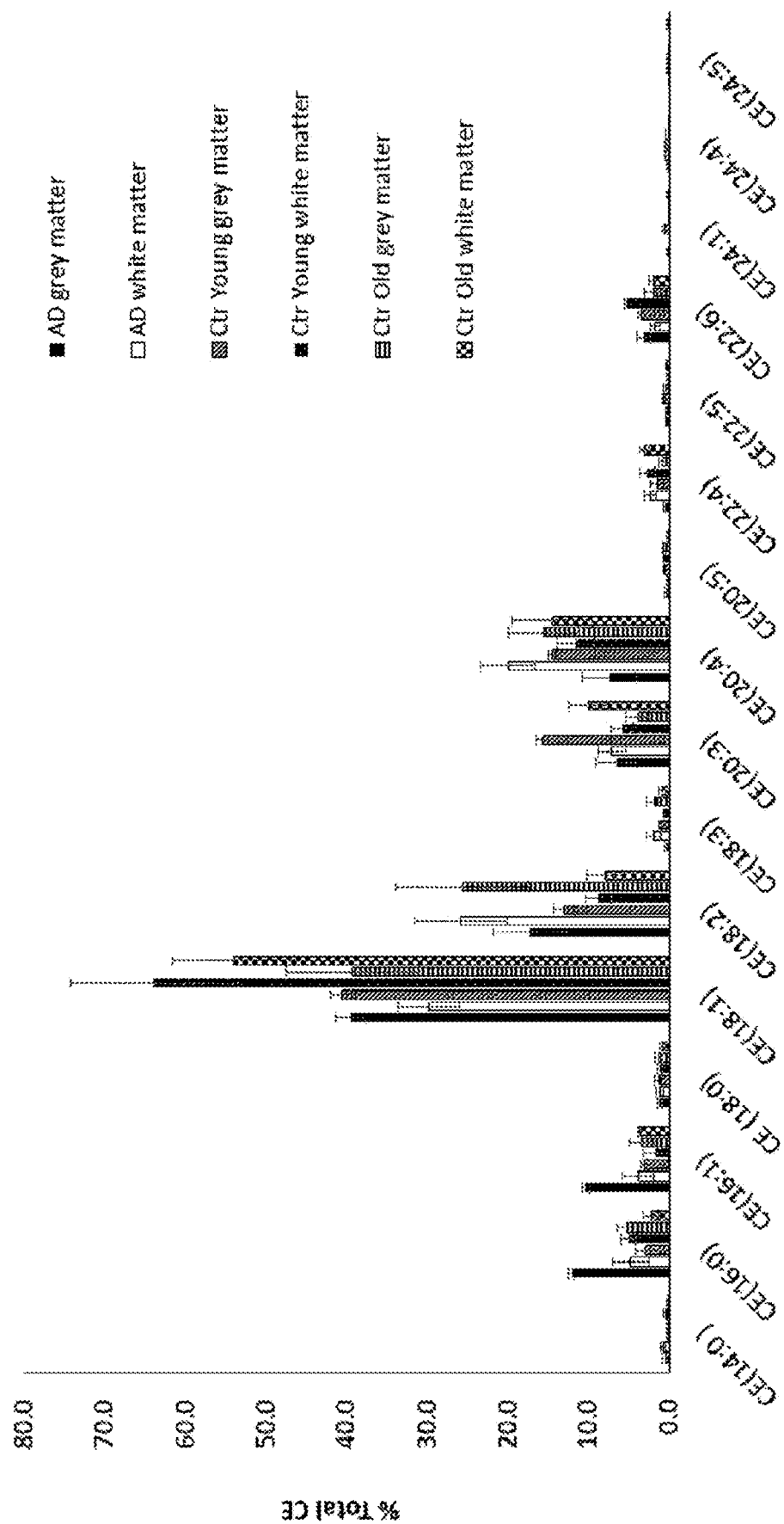

Yang, W., et al. "Memory Decline and Behavioral Inflexibility in Aged Mice Are Correlated With Dysregulation of Protein Synthesis Capacity," Front. Aging Neurosci. 11:246 (2019).

Attar A., et al., "A shortened Barnes Maze Protocol Reveals Memory Deficits at 4-months of age in the Triple-Transgenic Mouse Model of Alzheimer's Disease," PLOS ONE 8(11):e80355 (2013).

* cited by examiner

A)

B)

A)

B)

A)

B)

METHODS FOR EVALUATING AND IMPROVING COGNITIVE FUNCTION

CROSS REFERENCE TO RELATED APPLICATIONS

This application is a 371 National Stage entry of PCT Patent Application No. PCTAU2018/051207, filed Nov. 9, 2018, which claims the benefit of priority to Australian Patent Application No. 2017904551, filed Nov. 9, 2017.

FIELD OF THE INVENTION

The present invention generally relates to method for evaluating and improving cognitive function in a subject. In particular, the invention generally relates to methods for evaluating cognitive function in a subject by determining the level of specific cholesteryl esters in a subject, and to improving cognitive function in a subject comprising the administration of cholesteryl oleate, or analogues thereof.

BACKGROUND OF THE INVENTION

Cognitive function can be described as a subject's mental process that includes memory, attention, problem solving and mental imagery. A decrease in cognitive function may cause a noticeable and measurable decline in cognitive abilities, such as memory. Decreases in cognitive function that are serious enough to be noticed by the subjects experiencing them or to other people may indicate the presence of impaired cognitive function. Subjects with impaired cognitive function, especially impaired cognitive function involving in memory loss, are more likely to develop degenerative brain disorders such as dementia than subjects without impaired cognitive function.

Dementia is a descriptive term for a variety of degenerative brain disorders that results in reduced cognitive function and is associated with widespread reduction in the number of nerve cells and brain tissue shrinkage. Memory is the cognitive function most often affected by dementia. The memory loss may first manifest itself in simple absentmindedness, a tendency to forget or misplace things, or to repeat oneself in conversation. As the dementia progresses, the loss of memory broadens in scope until the patient can no longer remember basic social and survival skills and function independently. Dementia can also result in a decline in the patient's language skills, spatial or temporal orientation, judgment, or other cognitive capacities. Dementia tends to run an insidious and progressive course. Common types of dementia include Alzheimer's disease (AD), vascular dementia, frontotemporal dementia, dementia with lewy bodies, and other diseases such as Huntington's and prions disease.

Alzheimer's Disease (AD) is a degenerative brain disorder resulting in dementia and is presented clinically by progressive loss of cognitive function such as memory, cognition, reasoning, judgement, and emotional stability that gradually leads to profound-mental deterioration and ultimately death. Clinical presentation of AD is characterized by decrease in cognitive functions, such as memory, speech and reasoning.

Biomarkers that can be used to evaluate a subject's cognitive function, which may eventually lead to the diagnosis, monitoring the progression or regression of a degenerative brain disorder such as AD or dementia are in demand. However, reliable and non-invasive methods for diagnosing AD or dementia are not available. An early diagnosis of degenerative brain disorders such as AD or dementia has many advantages, including an increased time to benefit from treatment. Such treatments for degenerative brain disorders such as AD and/or dementia include psychotropic drugs and acetylcholinesterase inhibitors. However, these medications are often administered very cautiously to patients with dementia and in the lowest possible effective doses, owing to their toxicity, serious side effects, and/or requirement for supervision when administering the drugs to the subject.

There remains a need for reliable, preferably non-invasive, means for evaluating a subject's cognitive function which may result in the early diagnosis of a degenerative brain disorder such as AD or dementia. There also remains a need for further means for improving cognitive function.

SUMMARY OF THE INVENTION

The present inventors have identified that levels of cholesteryl esters, such as cholesteryl oleate, cholesteryl palmitate and cholesteryl palmitoleate, can be used to evaluate cognitive function in a subject. They have also identified methods of improving cognitive function in a subject comprising administering cholesteryl oleate or analogues thereof to a subject.

In one aspect, there is provided a method for evaluating cognitive function in a subject, the method comprising determining the level of cholesteryl oleate (CE 18:1) in the subject or a biological sample obtained therefrom, wherein a lower level of cholesteryl oleate is indicative of a greater level of impaired cognitive function.

In another aspect, the present invention provides a method of evaluating cognitive function in a subject, the method comprising determining the level of cholesteryl oleate (CE 18:1) in the subject or a biological sample obtained therefrom, wherein the lower the level of cholesteryl oleate the greater the likelihood of impaired cognitive function.

In some embodiments, the level of cholesteryl oleate (CE 18:1) in the subject or a biological sample obtained therefrom is compared to a reference level of cholesteryl oleate.

In some embodiments, the level of cholesteryl oleate lower than the reference level is indicative impaired cognitive function.

In some embodiments, the level of cholesteryl oleate in the subject or a biological sample obtained therefrom is monitored over time to detect changes in cognitive function.

In some embodiments, the cognitive function is memory.

In some embodiments, an impaired cognitive function is indicative of the presence, risk, progression and/or severity of a degenerative brain disorder. Examples of degenerative brain disorders include, but are not limited to, Alzheimer's disease (AD) or dementia.

In one embodiment, the level of cholesteryl oleate in the biological sample is indicative of the level of cholesteryl oleate in the brain of the subject. In another embodiment, the level of cholesteryl oleate in the biological sample is indicative of the level of cholesteryl oleate in the white matter frontal cortex of the brain of the subject.

In some embodiments, the biological sample obtained from the subject is selected from whole blood, blood plasma, blood serum, cerebrospinal fluid (CSF), mucus secretions and saliva. In one embodiment, the biological sample is whole blood.

In some embodiments, the level of cholesteryl oleate is determined using liquid chromatography/mass spectroscopy (LC/MS), gas chromatography-mass spectroscopy (GC/MS), mass spectroscopy (MS), liquid chromatography (LC), gas chromatography (GC), immunoblotting, ELISA assays, and protein microarrays, or combinations thereof. In one embodiment, the level of cholesteryl oleate is determined using liquid chromatography/mass spectrometry (LC/MS) analysis.

The inventors have also found that the levels of cholesteryl palmitate (CE 16:0) and cholesteryl palmitoleate (CE 16:1) can also be used to evaluate cognitive function in a subject. Accordingly, in another aspect there is provided a method for evaluating cognitive function in a subject, the method comprising determining the level of cholesteryl palmitate (CE 16:0) and/or cholesteryl palmitoleate (CE 16:1) in the subject or a biological sample obtained therefrom, wherein a higher level of cholesteryl palmitate and/or cholesteryl palmitoleate is indicative of a greater level of impaired cognitive function.

In some embodiments, the level of cholesteryl palmitate and/or cholesteryl palmitoleate in the subject or a biological sample obtained therefrom is compared to a reference level of cholesteryl oleate.

In some embodiments, the level of cholesteryl palmitate and/or cholesteryl palmitoleate higher than a reference level is indicative impaired cognitive function.

In some embodiments, the level of cholesteryl palmitate and/or cholesteryl palmitoleate in the biological sample is indicative of the level of cholesteryl oleate in the grey matter frontal cortex of the brain of the subject. Other embodiments as described above also apply to this aspect.

In some embodiments, if it is determined the subject is likely to have impaired cognitive function the subject is administered with a treatment for impaired cognitive function. In some embodiments, the treatment is an effective amount of an anti-Alzheimer's compound or an anti-dementia compound. In some embodiments, the treatment is an effective amount of cholesteryl oleate or an analogue thereof.

In a further aspect, the present invention provides a method for stratifying a group of subject's for a clinical trial of a candidate therapy for improving cognitive function, the method comprising evaluating cognitive function using a method of the invention, and using the results of the evaluation to select subject's more likely to be responsive to the therapy.

In yet another aspect, the present invention provides a method of placing a subject into an appropriate treatment category, the method comprising evaluating cognitive function using a method of the invention, and using the results of the evaluation to select the appropriate treatment category.

In another aspect, there is provided a method of improving cognitive function in a subject, the method comprising administering to the subject an effective amount of cholesteryl oleate, or an analogue thereof.

In some embodiments, the cholesteryl oleate, or analogue thereof is selected from lanosteryl oleate, dihydrolanosteryl oleate, zymosteryl oleate, zymostenyl oleate, lathosteryl oleate, 7-dehydrodesmosteryl oleate, 7-dehydrocholesteryl oleate, 8-dehydrocholesteryl oleate, desmosteryl oleate and cholesteryl oleate.

In some embodiments, the subject is administered with cholesteryl oleate which has the following structure:

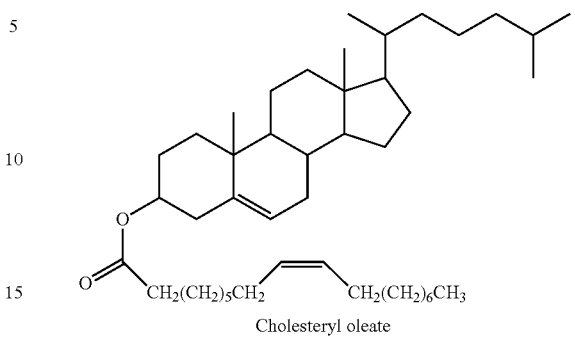

Cholesteryl oleate or a conjugate, salt or prodrug thereof.

In some embodiments, the cholesteryl oleate, or analogue thereof, is administered in the form of high-density lipoprotein (HDL) cholesterol.

In some embodiments, the cholesteryl oleate, or analogue thereof, is administered to the subject in an amount of about 1 mg to about 1 g per kg of bodyweight of the subject.

In some embodiments, the cholesteryl oleate, or analogue thereof, is provided as a nutraceutical composition.

In some embodiments, the cognitive function is memory. In some embodiments, the subject has been diagnosed with a degenerative brain disorder. The degenerative brain disorder may be Alzheimer's disease or dementia.

In some embodiments, the cholesteryl oleate, or analogue thereof, is the only cognitive enhancing therapeutically active ingredient administered to the subject. In some embodiments, the cholesteryl oleate, or analogue thereof, may be the only therapeutically active ingredient administered to the subject.

In another embodiment, cognitive function of the subject has been evaluated using a method of the present invention.

In another aspect, there is provided cholesteryl oleate, or an analogue thereof for use in improving cognitive function in a subject.

In another aspect, there is provided a use of cholesteryl oleate, or an analogue thereof, for the manufacture of a medicament or nutraceutical for improving cognitive function in a subject.

In another aspect, there is provided a pharmaceutical or nutraceutical composition comprising cholesteryl oleate, or an analogue thereof, and a pharmaceutically or nutraceutically acceptable excipient, wherein the cholesteryl oleate is present in an amount effective for improving cognitive function in a subject.

In some embodiments, the cholesteryl oleate, or an analogue thereof, in the pharmaceutical or nutraceutical composition is the selected from the group consisting of lanosteryl oleate, dihydrolanosteryl oleate, zymosteryl oleate, zymostenyl oleate, lathosteryl oleate, 7-dehydrodesmosteryl oleate, 7-dehydrocholesteryl oleate, 8-dehydrocholesteryl oleate, desmosteryl oleate and cholesteryl oleate.

In some embodiments, the cholesteryl oleate, or an analogue thereof, in the pharmaceutical or nutraceutical composition has the following structure:

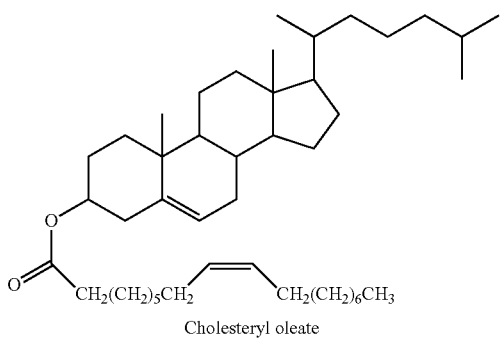

Cholesteryl oleate or a conjugate, salt or prodrug thereof.

In some embodiments, the cholesteryl oleate, or analogue thereof, is present in an amount of greater than 20% w/w of the pharmaceutical or nutraceutical composition.

In some embodiments, the cholesteryl oleate, or analogue thereof, is present in the pharmaceutical or nutraceutical in an amount so as to deliver to a subject about 1 mg to about 1 g of cholesteryl oleate, or an analogue thereof, per kg of bodyweight of the subject.

In some embodiments, at least some of the cholesteryl oleate or analogue thereof is in the form of high-density lipoprotein (HDL) cholesterol.

In some embodiments, the pharmaceutical or nutraceutical composition is in a form selected from an emulsion, a caplet, a capsule, a tablet, a gel, a serum, a bar, a powder, a spray, and a liquid.

In some embodiments, the pharmaceutical or nutraceutical composition is suitable to be administered orally, sublingually, nasally, or parenterally, or combinations thereof.

In some embodiments, the cholesteryl oleate, or analogue thereof, is the only cognitive enhancing therapeutically active ingredient in the pharmaceutical or nutraceutical composition. In some embodiments, the cholesteryl oleate, or analogue thereof, is the only therapeutically active ingredient in the pharmaceutical or nutraceutical composition.

In another aspect, there is provided a method of improving cognitive function in a subject, the method comprising administering to the subject an effective amount of cholesteryl oleate or a conjugate, salt or prodrug thereof.

In another aspect, there is provided cholesteryl oleate or a conjugate, salt or prodrug thereof, for use in a method for improving cognitive function in a subject.

In another aspect, there is provided a use of cholesteryl oleate or a conjugate, salt or prodrug thereof, for the manufacture of a medicament or nutraceutical for improving cognitive function in a subject.

In another aspect, there is provided a pharmaceutical or nutraceutical composition comprising cholesteryl oleate or a conjugate, salt or prodrug thereof.

In another aspect, there is provided a method of identifying a therapeutically effective compound for improving cognitive function in a subject, comprising administering an amount of a cholesteryl ester, or an analogue thereof, to an animal to determine if the animal has improved cognitive function.

In some embodiments, the cholesteryl ester, or an analogue thereof, administered to the animal to determine if the animal has improved cognitive function is a compound according to Formula 1:

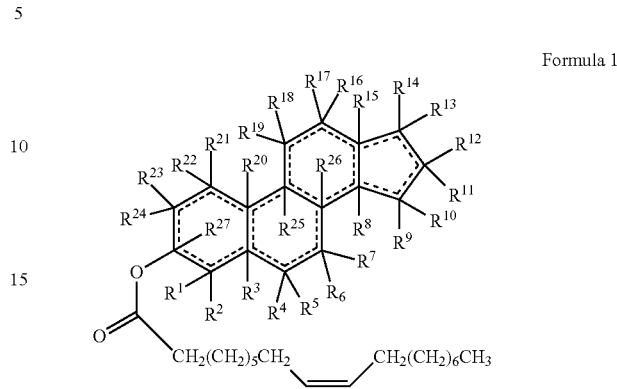

Formula 1 or a conjugate, salt or prodrug thereof,
wherein
===== represents a single or double bond;
$R^1$ to $R^{27}$ are each either absent or independently selected from the group consisting of hydrogen, alkyl, and alkenyl, wherein each alkyl and alkenyl is optionally substituted with the one or more alkyl. In some embodiments, $R^1$ to $R^{27}$ are each either absent or independently selected from the group consisting of hydrogen, $C_{1-12}$alkyl, and $C_{2-12}$alkenyl, wherein each $C_{1-12}$alkyl and $C_{2-12}$ alkenyl is optionally substituted with the one or more $C_{1-12}$alkyl.

In some embodiments, the cholesteryl ester, or an analogue thereof, administered to the animal to determine if the animal has improved cognitive function is a compound according to Formula 1a:

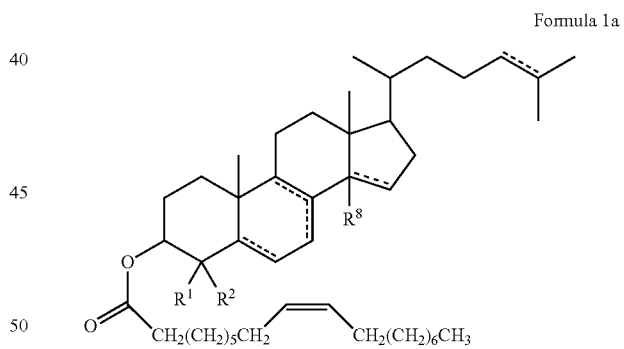

Formula 1a or a conjugate, salt or prodrug thereof,
wherein
===== represents a single or double bond;
$R^1$ and $R^2$ are each independently hydrogen or $C_{1-12}$alkyl; and
$R^8$ is either absent or hydrogen or $C_{1-12}$ alkyl.

In some embodiments, $R^1$ and $R^2$ are each independently hydrogen or $C_{1-6}$alkyl, and $R^8$ is either absent or hydrogen or $C_{1-6}$alkyl.

In some embodiments, $R^1$ and $R^2$ are each independently hydrogen or methyl, and $R^8$ is either absent or hydrogen or methyl.

Any embodiment herein shall be taken to apply mutatis mutandis to any other embodiment unless specifically stated otherwise.

The present invention is not to be limited in scope by the specific embodiments described herein, which are intended for the purpose of exemplification only.

Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following description and non-limiting Examples and with reference to the accompanying figures.

BRIEF DESCRIPTION OF THE ACCOMPANYING DRAWINGS

FIG. 1: Percentage of total cholesteryl ester in the grey matter and white matter of the human brain frontal cortex.

Figure 2:
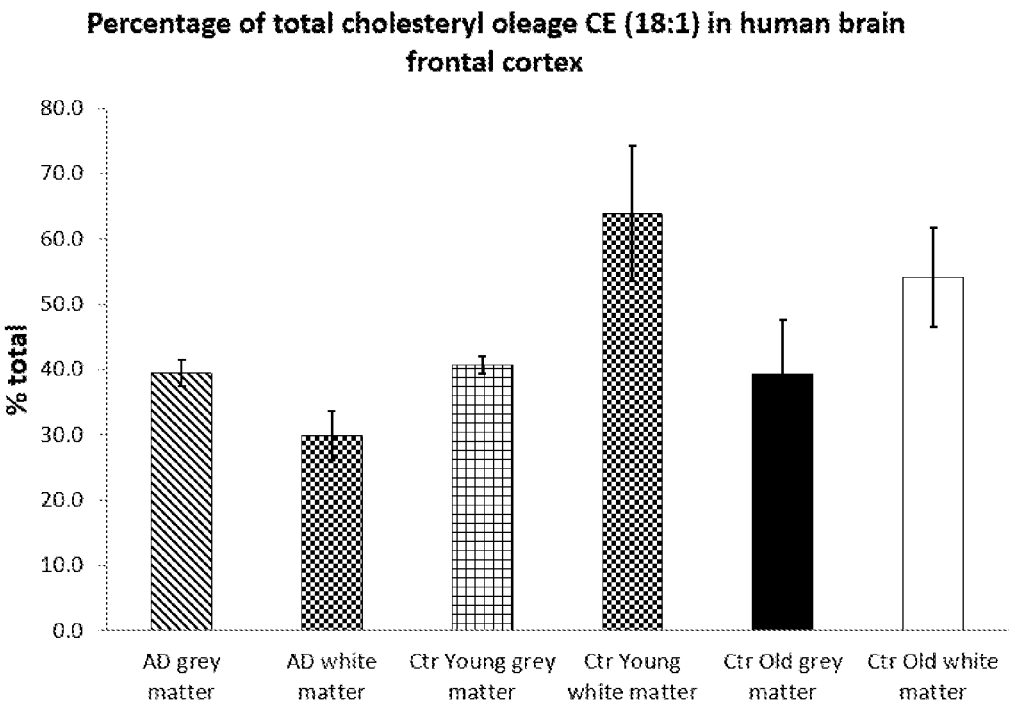
Figure 2:
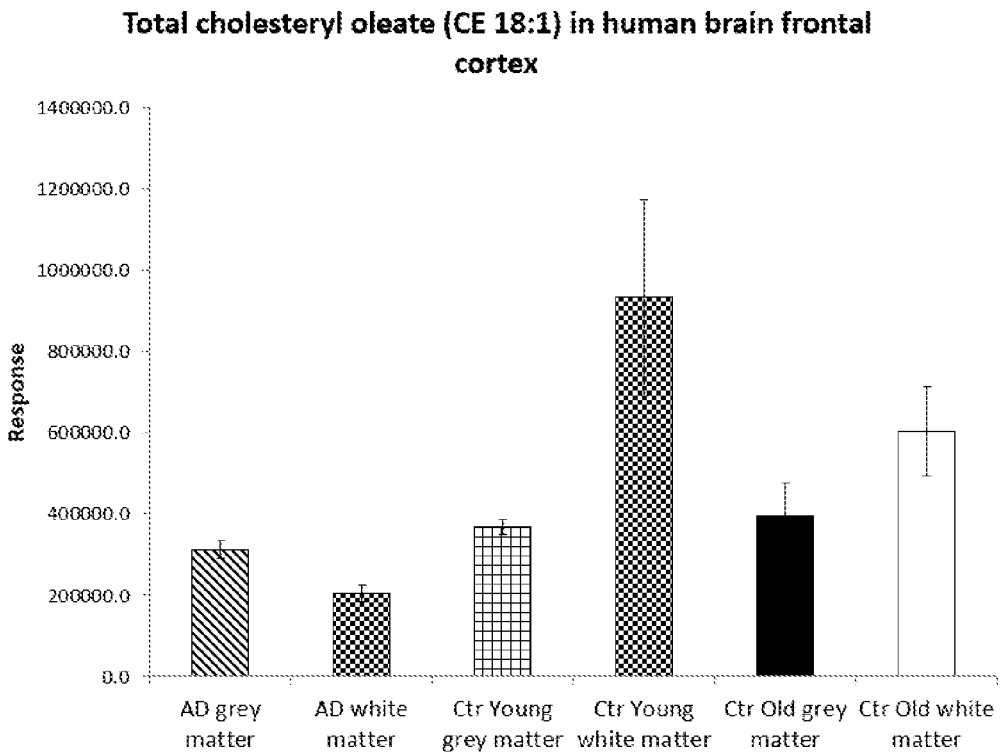

FIG. 2: Effect of ageing and cognitive function on levels of cholesteryl oleate (CE 18:1) in the human brain frontal cortex. The levels of CE 18:1 were obtained from the grey and white matter of patients with Alzheimer's disease (AD); control young subjects, and control old subjects (AD patient=75 year old male; control young subject=25 year-old healthy male; control old subject=75 year-old healthy male). A) Relative levels, B) Absolute levels.

Figure 3:
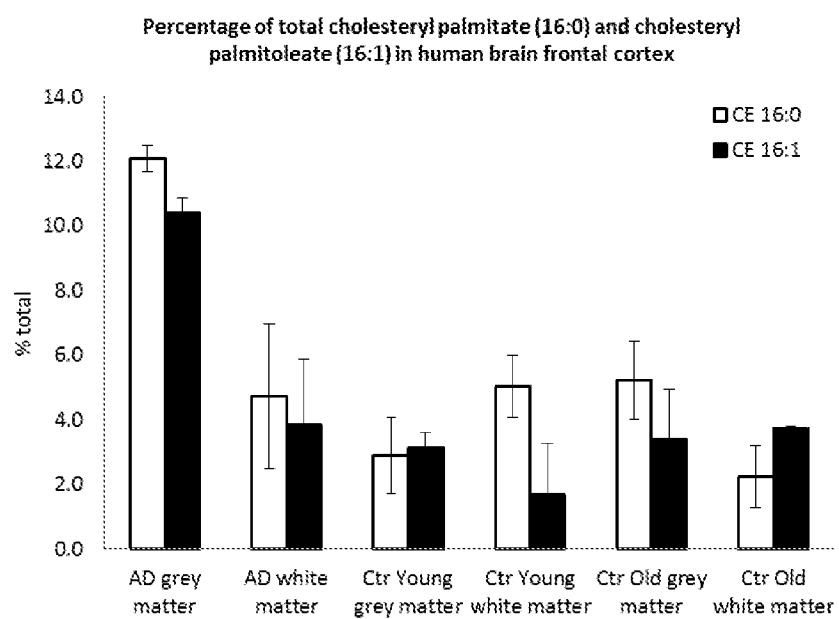

FIG. 3: Effect of ageing and cognitive function on relative levels of cholesteryl palmitate (CE 16:0) and cholesteryl palmitoleate (CE 16:1) in the human brain frontal cortex. The levels of CE 16:0 and CE 16:1 were obtained from the grey and white matter of patients with Alzheimer's disease (AD); control young subjects, and control old subjects (AD patient=75 year old male; control young subject=25 year-old healthy male; control old subject=75 year-old healthy male).

Figure 4:
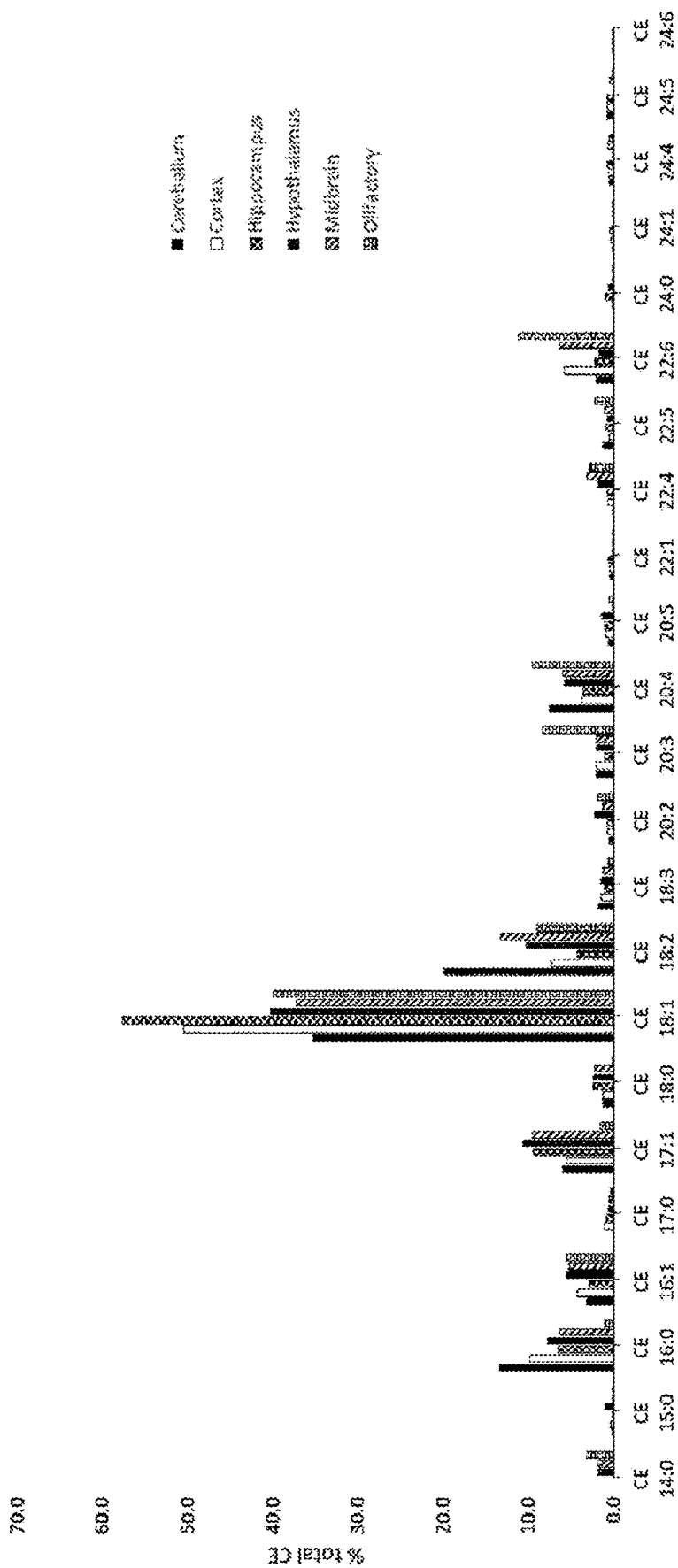

FIG. 4: Percentage of total cholesteryl ester in brain of young mouse (3 months old).

Figure 5:
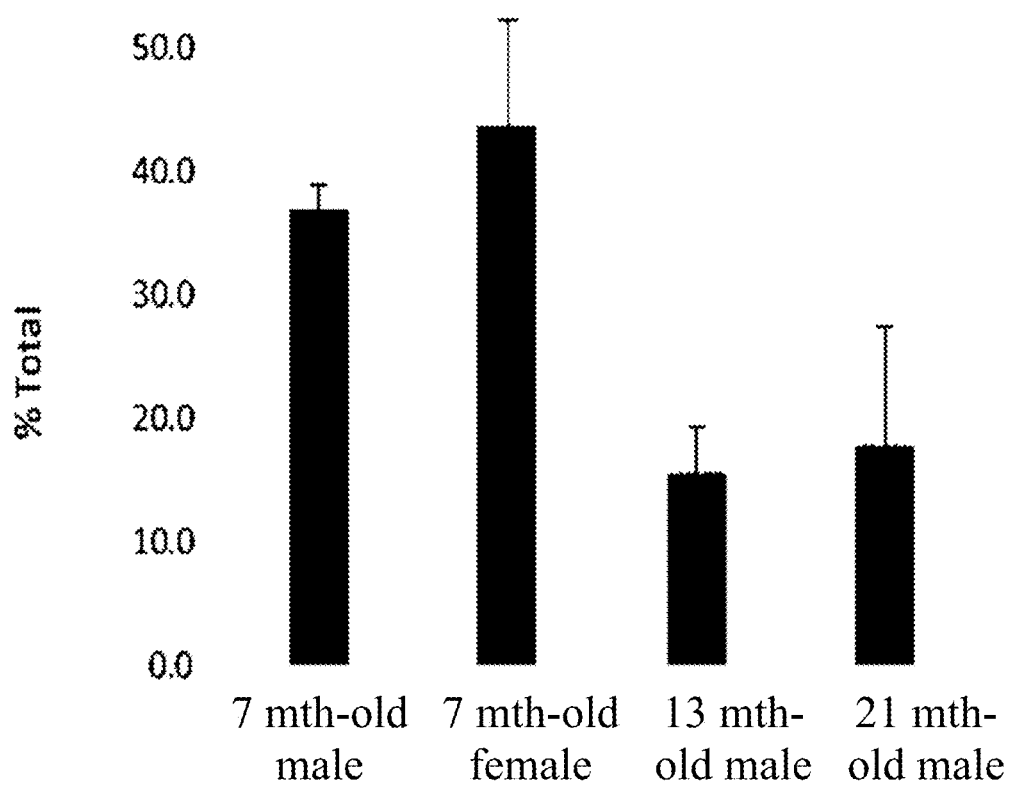

FIG. 5: Effect of ageing on levels of cholesteryl oleate (CE 18:1) in mice. The levels of CE 18:1 in mice brain frontal cortex were obtained from young mice (7 months old) and old mice (13 months old and 21 months old).

Figure 6:
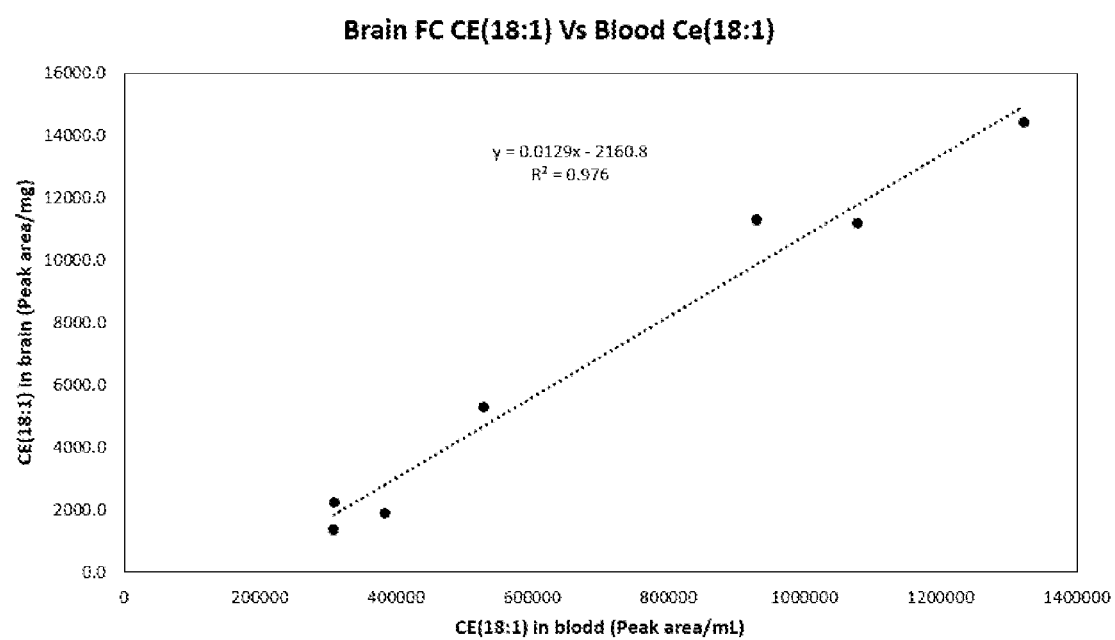

FIG. 6: Correlation between levels of cholesteryl oleate (CE 18:1) in whole blood and the levels of cholesteryl oleate (CE 18:1) in brain frontal cortex white matter of mice.

Figure 7:
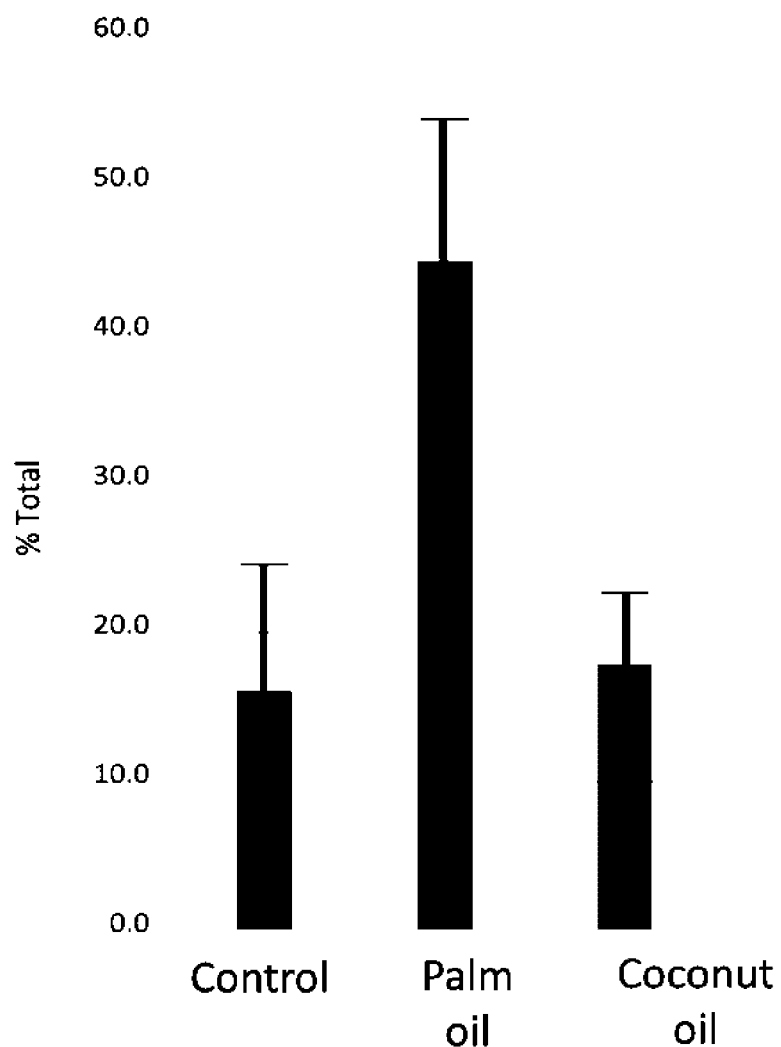

FIG. 7: Effect of oleic acid enriched diet (palm oil) on the levels of cholesteryl oleate (CE 18:1) in brain frontal cortex in old mice (19-21 month old mice) compared with a non-oleic acid enriched diet (control)

Figure 8:
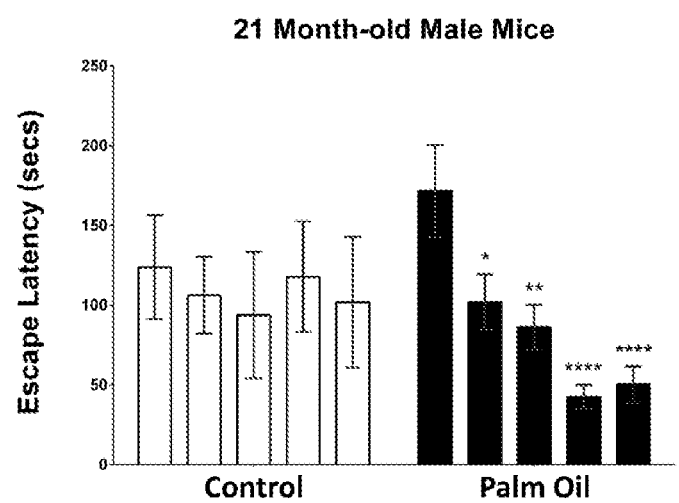

FIG. 8: Effect of oleic acid enriched diet (palm oil) on escape latency (seconds) in old mice (21 months) compared to a non-oil supplemented diet (i.e. non-oleic acid enrichment) and a coconut oil supplemented diet (enriched with other fatty acids, but not oleic acid).

Figure 9:
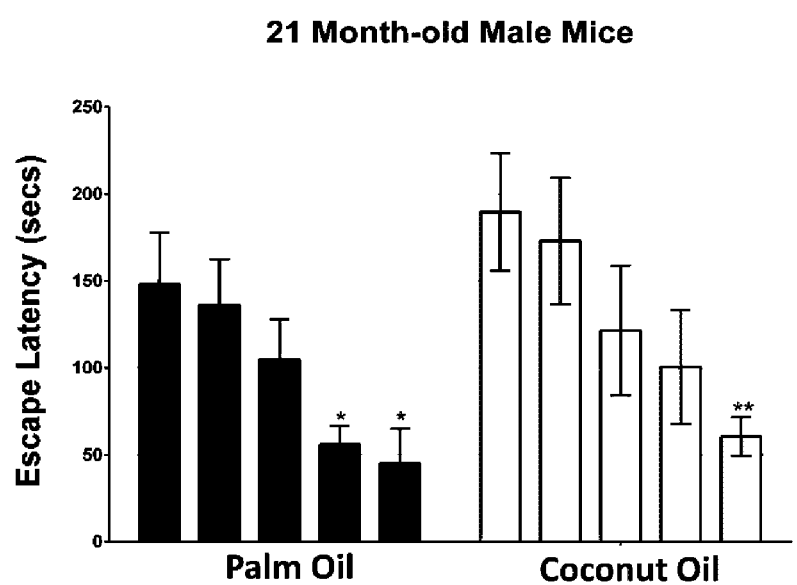

FIG. 9: Effect of palm oil supplemented diet (oleic acid enrichment) on escape latency (seconds) in old mice (21 months) compared to a coconut oil supplemented diet (enriched with other fatty acids, but not oleic acid).

Figure 10:
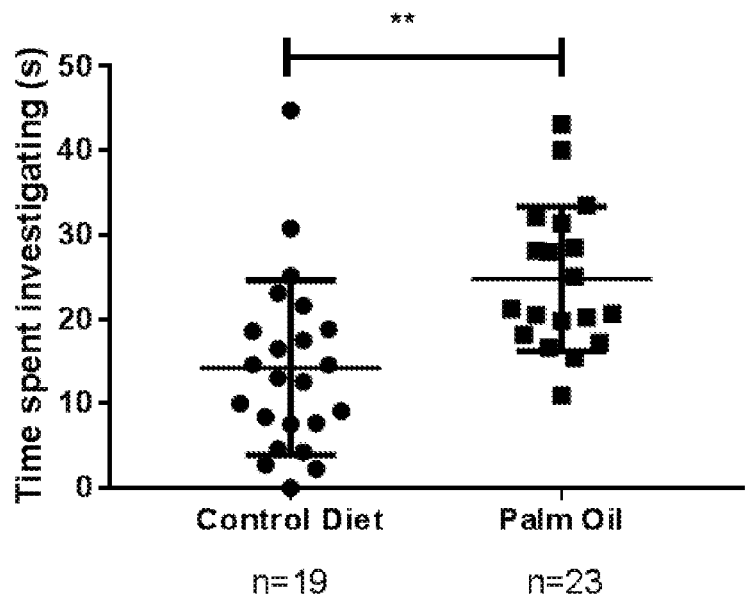
Figure 10:
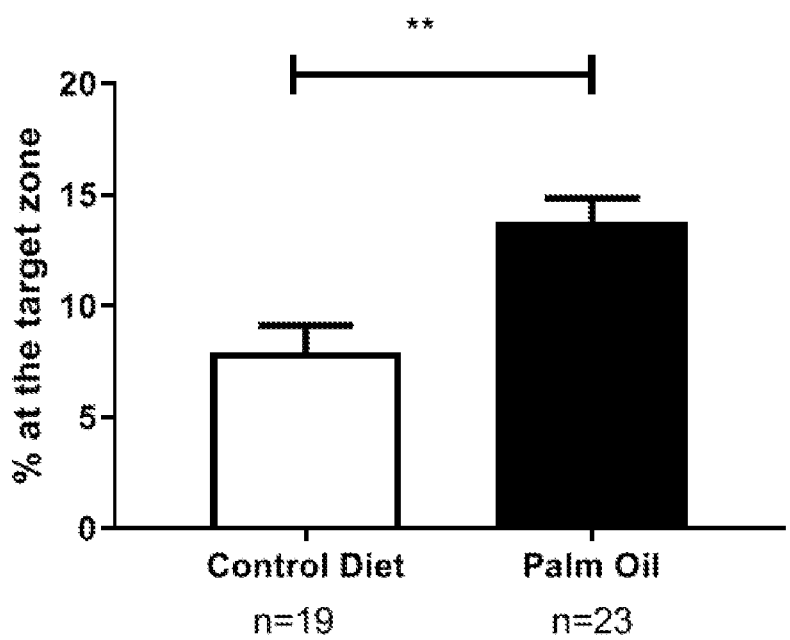

FIG. 10: Effect of palm oil supplemented diet (oleic acid enrichment) on the time spent investigating the target zone in the Barnes Maze in old mice (21 months) compared to a control diet (no oleic acid enrichment).

Figure 11:
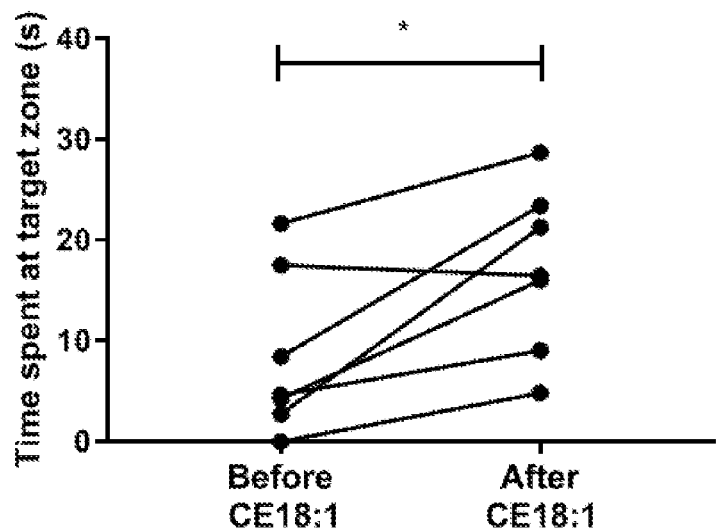
Figure 11:
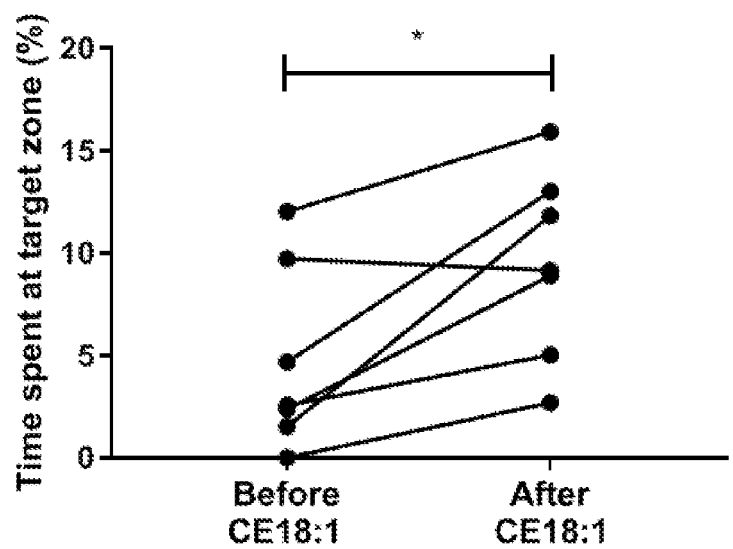

FIG. 11: Effect of cholesteryl oleate (CE 18:1) administration on the time spent investigating the target zone in the Barnes Maze in old mice (24 months).

Figure 12:
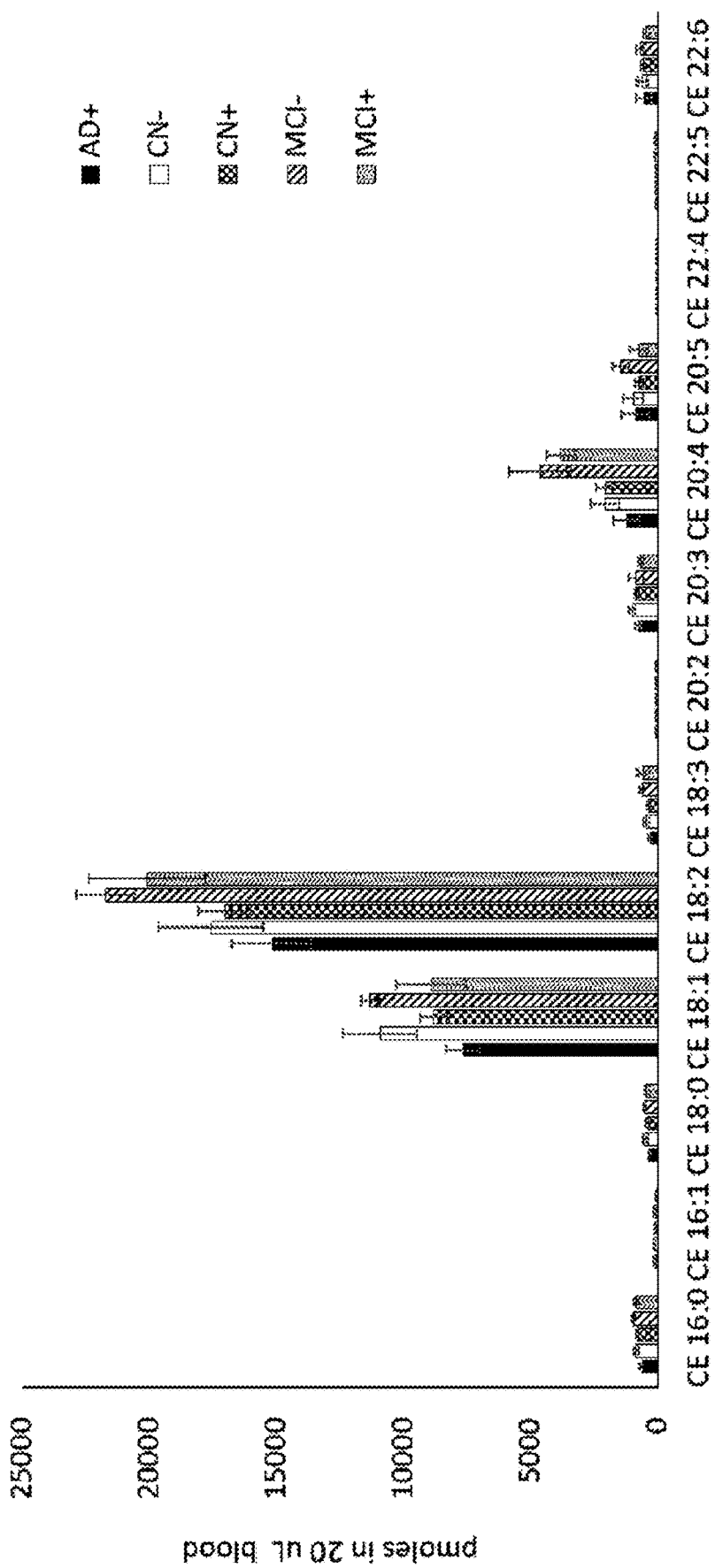

FIG. 12: Total amount of cholesteryl ester in human blood matter of patients (picomoles in 20 μmL blood): (AD+) Alzheimer's disease patients with beta-amyloid plague detected in the brain by MRI; (CN−) cognitive normal control with no detectable beta-amyloid plague; (CN+) cognitive normal control with beta-amyloid plague detected in the brain by MRI; (MCI−) mild cognitive impaired patients with no detectable beta-amyloid plague; (MCI+) mild cognitive impaired patients with beta-amyloid plague detected in the brain by MRI.

Figure 13:
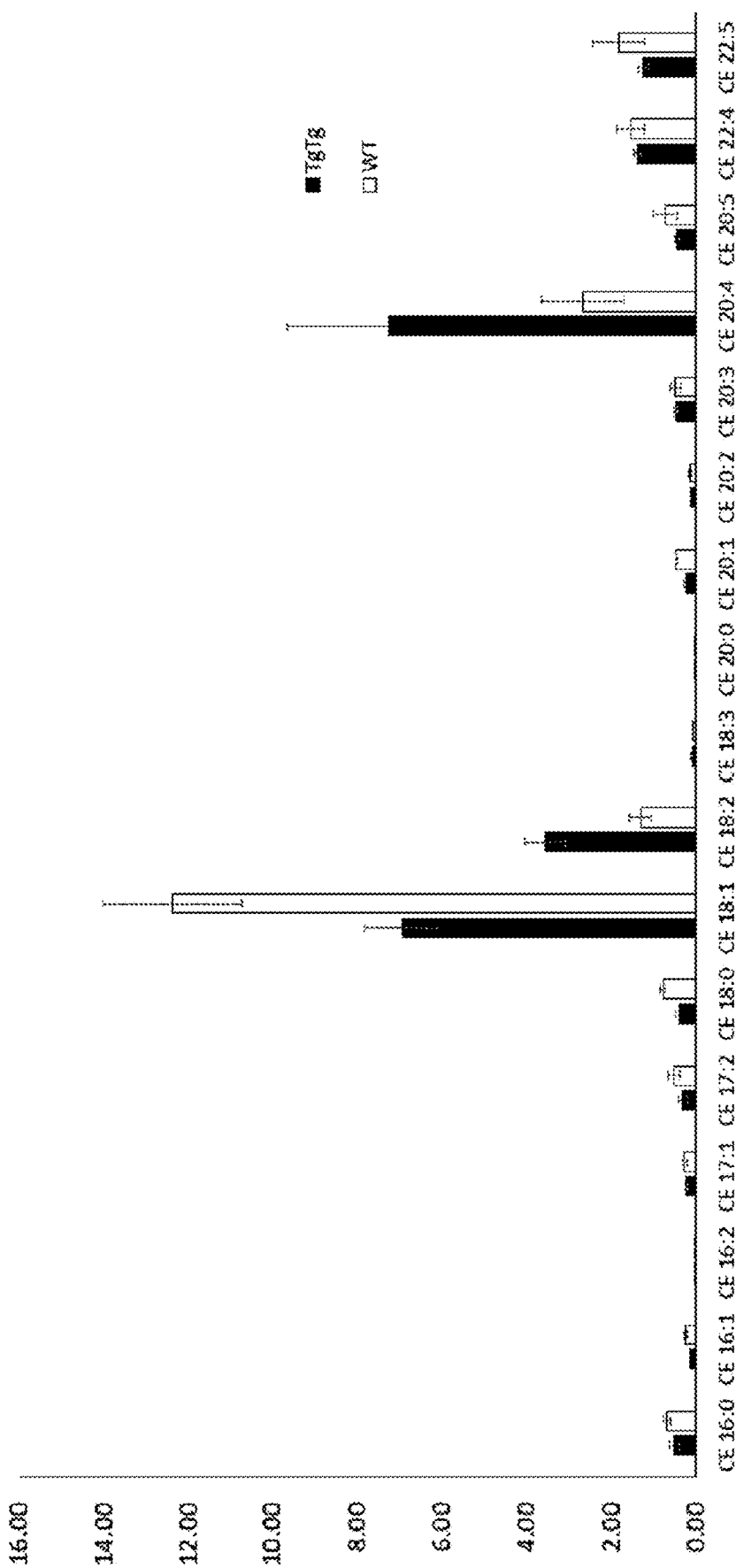

FIG. 13: Percentage of cholesteryl ester from whole brain assay in APP/PS1 transgenic 12 week-old female mouse brain (TgTg) compared with sex and age matched wild type (WT).

Figure 14:
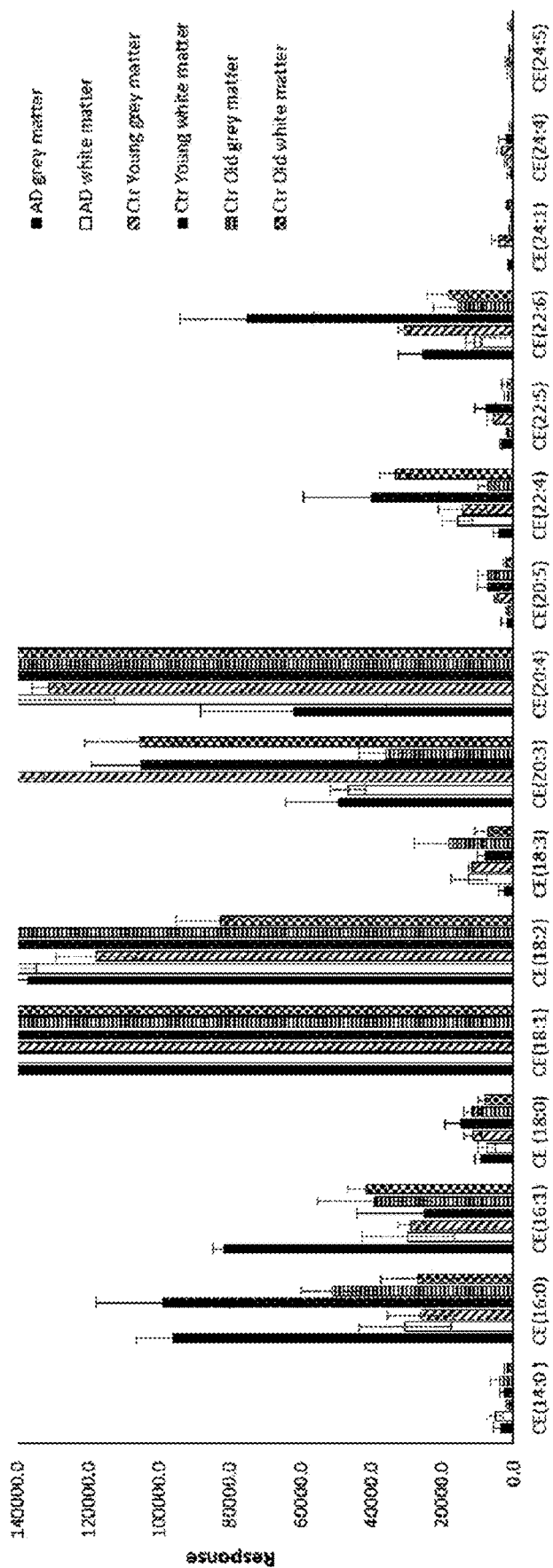

FIG. 14: Percentage of total cholesteryl ester in the grey matter and white matter of the human brain frontal cortex magnified from FIG. 1.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., cognitive function, cognitive impairment, and formulation and detection of cholesterol-fatty acid esters).

As used herein, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

As used herein, the term "about", unless stated to the contrary, refers to +/−10%, more preferably +/−5%, even more preferably +/−1%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the terms "treatment" or "treating" or variations thereof refers to the alleviation, prevention or elimination of one or more symptoms associated with impaired cognitive function.

As would be understood by the person skilled in the art, a treatment such as cholesteryl oleate or analogue thereof would be administered in an effective amount. As used herein, the term "effective amount" or "therapeutically effective amount", refers to a treatment such as cholesteryl oleate or analogue thereof being administered in an amount sufficient to alleviate prevent or eliminate one or more of the symptoms of the disorder or condition being treated, such as impaired cognitive function, Alzheimer's disease and/or dementia. The result can be the reduction and/or alleviation of the signs, symptoms, or causes of a disease or condition, or any other desired altercation of a biological system. For example, one result may be the reduction and/or alleviation of symptoms of impaired cognitive function, Alzheimer's disease and/or dementia. With regard to some embodiments of the present disclosure, the term, an "effective amount", as used herein, refers to an amount of cholesteryl oleate or analogue thereof to achieve a desired pharmacologic effect or therapeutic improvement without undue adverse side effects, for example improved cognitive function. By way of example only, therapeutically effective amounts may be determined by routine experimentation, including but not limited to a dose escalation clinical trial. It is understood that "an effective amount" or "a therapeutically effective amount" can vary from subject to subject, due to variation in metabolism of the compound and any of age, weight, general condition of the subject, the condition being treated, the severity of the condition being treated, and the judgment of the prescribing physician. Thus, it is not always possible to specify an exact "effective amount". However, an appropriate "effective amount" in any individual case may be determined by the person skilled in the art using routine experimentation.

As used herein, the term "therapeutically active ingredient" refers to an agent, active ingredient compound or other substance, that provides some pharmacological, often beneficial, effect. For example, the therapeutically active ingredient may increase cognitive function. Reference to a specific active ingredient shall include where appropriate the active ingredient and it's pharmaceutically acceptable salts. The term "cognitive enhancing therapeutically active ingredient" refers to an agent, active ingredient compound or other substance, where upon administration to a subject, may improve their cognitive function.

As used herein, the term "optionally substituted" means that a functional group is either substituted or unsubstituted, at any available position. It will be understood that the term "optionally substituted" in the context of the present disclosure, includes the substituents alkyl, alkenyl and alkynyl, as described herein below.

As used herein, the term "alkyl" represents straight or branched chain hydrocarbons ranging in size from one to about 20 carbon atoms, or more. Thus alkyl moieties include, unless explicitly limited to smaller groups, moieties ranging in size, for example, from one to about 6 carbon atoms or greater, such as, methyl, ethyl, n-propyl, iso-propyl and/or butyl, pentyl, hexyl, and higher isomers, including, e.g., those straight or branched chain hydrocarbons ranging in size from about 6 to about 20 carbon atoms, or greater. In one example, the alkyl moiety is of one to 12 carbon atoms.

As used herein, the term "alkenyl" represents straight or branched chain hydrocarbons containing at least one carbon-carbon double bond, including, unless explicitly limited to smaller groups, moieties ranging in size from two to about 6 carbon atoms or greater, such as, methylene, ethylene, 1-propenyl, 2-propenyl, and/or butenyl, pentenyl, hexenyl, and higher isomers, including, e.g., those straight or branched chain hydrocarbons ranging in size, for example, from about 6 to about 20 carbon atoms, or greater. In one example, the alkenyl moiety is of two to 12 carbon atoms.

As used herein, the term "$C_{1-12}$alkyl, refers to a straight chain or branched, saturated hydrocarbon having from 1 to 12 carbon atoms. Representative "$C_{1-12}$alkyl" groups include, but are not limited to, -methyl, -ethyl, -n-propyl, -n-butyl, -n-pentyl, -n-hexyl, -n-heptyl, -n-octyl, -n-nonyl, -n-decyl, n-undecyl, and n-dodecyl; while branched $C_1$-$C_{12}$ alkyls include, but are not limited to, -isopropyl, -sec-butyl, -isobutyl, -tert-butyl, 2-methylbutyl. $C_1$-$C_{12}$ alkyls include, but are not limited to, 1-hexyl, 2-hexyl, 3-hexyl, methyl, ethyl, propyl, isopropyl, n-butyl, isobutyl, sec-butyl, tert-butyl, n-pentyl, isopentyl, neopentyl, n-hexyl, isohexyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 6-methylheptan-2-yl, 3-methylheptyl, n-heptyl, isoheptyl, n-octyl, and isooctyl. A $C_1$-$C_{12}$ alkyl group can be unsubstituted or optionally substituted with one or more $C_1$-$C_{12}$ alkyl.

As used herein, the term "$C_{2-12}$alkyenyl," refers to a straight chain or branched, unsaturated hydrocarbon having from 2 to 12 carbon atoms containing at least one carbon-carbon double bond. Representative "$C_{2-12}$alkyl" groups include, but are not limited to, -ethenyl, -n-propenyl, -n-butenyl, -n-pentenyl, -n-hexenyl, -n-heptenyl, -n-octenyl, -n-nonenyl, -n-decenyl, n-undecenyl, and n-dodecenyl Representative "$C_{2-12}$alkenyl" groups include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, and -acetylenyl, A $C_2$-$C_{12}$ alkenyl group can be unsubstituted or optionally substituted with one or more $C_1$-$C_{12}$ alkyl.

As used herein, the term " ===== " refers to a single or double bond. Unless indicated otherwise, the single or double bond occurs between two neighbouring carbon atoms. For example, " ===== " may represent a single —C—C— bond, or " ===== " may represent a —C═C— bond. The person skilled in the art would understand that compounds according to Formula 1 and Formula 1a disclosed herein will satisfy each carbon atoms correct valency requirements, i.e. that a neutral carbon atom has 4 valence electrons (i.e. tetravalent) which are available for covalent bonding. By way of example, a carbon atom can form four covalent bonds by pairing its four valence electrons with four electrons from other atoms. This includes, for example, forming bonds to other carbon atoms. By way of example only, when referring to Formula 1a below:

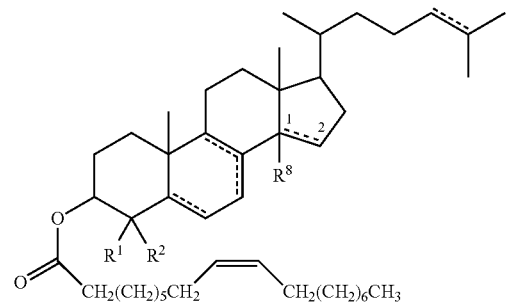

where a —C═C— double bond is present between carbons at positions 1 and 2 in the central ring structure, the person skilled in the art would understand that $R^8$ is absent, and that one of the hydrogens present at the carbon at position 2 will also be absent, and therefore satisfy the valency requirements of the carbon atoms at positions 1 and 2. As a further example, where a —C—C— single bond is present between carbons at positions 1 and 2, the person skilled in the art would understand that $R^8$ is present, and may be selected from the possible substituents as defined throughout the specification (i.e. hydrogen or $C_{1-12}$alkyl), along with two hydrogens being present at position 2.

In one example, a —C═C— double bond is present between carbons at positions 1 and 2 of Formula 1a, and $R^8$ is absent, for example:

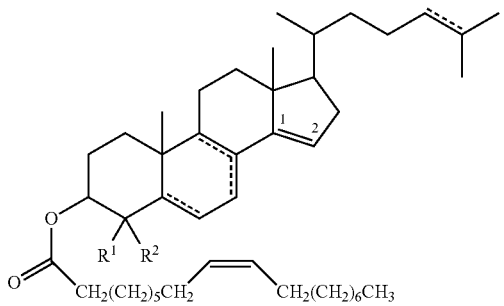

In another example, a —C—C— single bond is present between carbons at positions 1 and 2 of Formula 1a, and $R^8$ is present, and is selected from hydrogen or $C_{1-12}$alkyl (i.e. methyl), for example

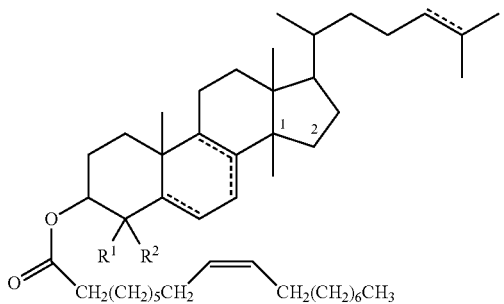

The person skilled in the art would also understand that where ═════ outlines a —C═C— double or —C—C— single bond in the structures of Formulas 1 or 1a, that an appropriate choice is made so as to satisfy the valency requirements of the carbon atoms in the central ring structure.

As used herein, the term "analogue" means a chemical compound which retains the parent structure as a substructure, but differing from it in respect of a certain component. For example, in some embodiments the analogue may be an analogue of cholesteryl oleate as defined herein. By way of example only, a cholesteryl oleate analogue may retain the androstane or estrane parent structure of cholesterol but may differ in respect of certain components. For example, an analogue of cholesteryl oleate may be selected from those compounds that are naturally present in the lanosterol to cholesterol biosynthesis pathway, which would be understood by the person skilled in the art.

As used herein, the term "conjugate" refers to a compound formed by the joining of two or more chemical compounds. For example, high-density lipoprotein (HDL) which may comprise cholesteryl oleate may be considered a conjugate, which upon administration to the subject, releases cholesteryl oleate.

As used herein, the term "prodrug" refers to any compound which, when administered to a subject, is converted in whole or in part to a cholesteryl oleate or an analogue thereof, as defined herein.

As used herein, the phrase "salt" refers to any pharmaceutically acceptable organic or inorganic salts. Salts may include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A salt may involve the inclusion of another molecule such as an acetate ion, a succinate ion or other counterion. The counterion may be any organic or inorganic moiety that stabilizes the charge on the parent compound. Furthermore, a salt may have more than one charged atom in its structure. Instances where multiple charged atoms are part of the salt can have multiple counter ions. Hence, a salt can have one or more charged atoms and/or one or more counterion.

Method for Evaluating Cognitive Function

The present disclosure relates to a method for evaluating cognitive function in a subject. The present inventors have discovered that by determining the level of cholesteryl esters in a subject or biological sample obtained therefrom, that the cognitive function of the subject was able to be assessed.

In some embodiments, the method involves determining the level of one or more cholesteryl esters in the subject or a biological sample obtained therefrom, preferably in a manner which is non-invasive, and offers a reliable and/or alternative means for evaluating a subject's cognitive function compared to other methods of evaluating cognitive function.

In one embodiment, the cholesteryl ester is cholesteryl oleate (CE 18:1). In another embodiment, the cholesteryl ester is cholesteryl palmitate (CE 16:0) and/or cholesteryl palmitoleate (CE 16:1).

In some embodiments, by determining the level of cholesteryl oleate (CE 18:1) in a subject or biological sample obtained therefrom, the cognitive function of the subject was able to be assessed. In other embodiments, by determining the level of cholesteryl palmitate (CE 16:0) and/or cholesteryl palmitoleate (CE 16:1) in a subject or biological sample obtained therefrom, the cognitive function of the subject was able to be assessed.

In some embodiments, the method involves determining the level of cholesteryl oleate (CE 18:1) in the subject or a biological sample obtained therefrom, preferably in a manner which is non-invasive, and offers a reliable and/or alternative means for evaluating a subject's cognitive function compared to other methods of evaluating cognitive function. In other embodiments, the method involves determining the level of cholesteryl palmitate (CE 16:0) and/or cholesteryl palmitoleate (CE 16:1) in the subject or a biological sample obtained therefrom, preferably in a manner which is non-invasive, and offers a reliable and/or alternative means for evaluating a subject's cognitive function compared to other methods of evaluating cognitive function.

In some embodiments, there is provided a method of evaluating cognitive function in a subject, the method comprising determining the level of cholesteryl oleate (CE 18:1) in the subject or a biological sample obtained therefrom, wherein a lower level of cholesteryl oleate is indicative of a greater level of impaired cognitive function. For example, referring to FIG. 2, the level of CE 18:1 in the brain of a subject varies significantly with the subject's cognitive function. In particular, it has been identified that the levels of CE 18:1 in the brain's white matter of subjects suffering from Alzheimer's disease is statistically less than the levels of CE 18:1 in both control young and old subjects who are not suffering from Alzheimer's disease.

In other embodiments, there is provided a method of evaluating cognitive function in a subject, the method comprising determining the level of cholesteryl palmitate (CE 16:0) and/or cholesteryl palmitoleate (CE 16:1) in the subject or a biological sample obtained therefrom, wherein a higher level of cholesteryl palmitate and/or cholesteryl palmitoleate is indicative of a greater level of impaired cognitive function. For example, referring to FIG. 3, the level of CE 16:0 and CE 16:1 in the grey matter of subjects suffering from Alzheimer's disease is statistically higher than both the levels of CE 16:0 and CE 16:1 in the grey matter of control young and old subjects.

In some embodiments, the ratio of cholesteryl esters in the subject or a biological sample obtained therefrom, may be used to evaluate the subjects cognitive function. For example, the ratio of cholesteryl oleate (CE 18:1) to cholesteryl palmitoleate (CE 16:1) may be used as an indicator of impaired cognitive function. For example, in some embodiments, where the level of cholesteryl ester in a subject is being monitored over time, a decrease in the cholesteryl oleate (CE 18:1):cholesteryl palmitoleate (CE 16:1) ratio may indicate a greater level of impaired cognitive function. Alternatively, in some embodiments, where the level of cholesteryl ester in a subject is being monitored over time, an increase in cholesteryl oleate (CE 18:1); cholesteryl palmitoleate (CE 16:1) ratio may indicate an improvement in cognitive function.

The "cognitive function" in the subject may be any cognitive function which will be understood by the person skilled in the art as any mental process. For example, the cognitive function in a subject may be, but is not limited to, the subject's memory, attention, problem solving and/or mental imagery. For example, in some embodiments, the subjects cognitive function is memory. As will be understood by the person skilled in the art, memory is the cognitive function by which a subject's mind stores and remembers information.

As used herein, the term "evaluating cognitive function" refers to measuring, reviewing and/or analysing a patient's cognitive function. In this regard, the present inventors have found that cholesteryl esters can act as a marker for cognitive function. In some embodiments, cholesteryl oleate is a marker for cognitive function, where low levels of cholesteryl oleate (CE 18:1) are indicative of impaired cognitive function. In other embodiments, cholesteryl palmitate (CE 16:0) and/or cholesteryl palmitoleate (CE 16:1) is a marker for cognitive function, where high levels of cholesteryl palmitate and/or cholesteryl palmitoleate are indicative of impaired cognitive function.

As used herein, the term "impaired cognitive function" in a subject refers to any decline in cognitive function which is greater than the expected decline of cognitive function associate with normal aging. For example, impaired cognitive function may refer to a decrease in the subject's memory, attention, problem solving and/or mental imagery which is greater than the expected decrease associated with normal aging. For example, in some embodiments, an impaired cognitive function is a decrease in memory. In some embodiments, a subject having impaired cognitive function is indicative of the presence, risk, progression and/or severity of a degenerative brain disorder in the subject. In some embodiments, the degenerative brain disorder may be selected from either Alzheimer's disease (AD) or dementia, wherein the dementia is selected from the group consisting of vascular dementia, frontotemporal dementia, dementia with lewy bodies, and other diseases such as Huntington's and prions disease. In some embodiments, the degenerative brain disorder is Alzheimer's disease (AD). In another embodiment, the degenerative brain disorder is dementia. It will be understood for the purposes of this invention, that term "dementia" encompasses all types of dementia other than Alzheimer's disease (AD).

As used herein, the term "improving cognitive function" refers to activating, increasing, stabilizing, maintaining, enhancing or restoring cognitive function in a subject.

As used herein, "obtained" or "obtaining" or variations there can be any means whereby one comes into possession of the sample by "direct" or "indirect" means. Directly obtaining a sample means performing a process (e.g., performing a physical method such as extraction) to obtain the sample from a subject. Directly obtaining a sample includes performing a process that includes a physical change in a physical substance, e.g., a starting material, such as a blood, e.g., blood that was previously isolated from a subject. Thus, obtain is used to mean collection and/or removal of the sample from the subject. Indirectly obtaining a sample refers to receiving the sample from another party or source (e.g., a third party laboratory that directly acquired the sample).

In some embodiments, the subject is a mammal. In an embodiment, the subject is a human. Examples of a "subject" include, but are not limited to, a human, rat, mouse, guinea pig, monkey, pig, goat, cow, horse, dog, cat, bird and fowl. In an exemplary embodiment, the subject is a human. Examples of an "animal" include, but are not limited to, a human, rat, mouse, guinea pig, monkey, pig, goat, cow, horse, dog, cat, bird and fowl. In an exemplary embodiment, the animal is a mouse.

The biological sample obtained from the subject can be any material or tissue that has levels of the cholesteryl ester which are indicative of the levels of the cholesteryl ester being determined in the brain. In some embodiments, the biological sample obtained from the subject can be any material or tissue that has levels of cholesteryl oleate which are indicative of the levels of cholesteryl oleate in the brain, in particular the levels of cholesteryl oleate in the white matter of the frontal cortex of the brain.

In other embodiments, the biological sample obtained from the subject can also be any material or tissue that has levels of cholesteryl palmitate and/or cholesteryl palmitoleate which are indicative of the levels of cholesteryl palmitate and/or cholesteryl palmitoleate in the brain, in particular the levels of cholesteryl palmitate and/or cholesteryl palmitoleate in the grey matter of the frontal cortex of the brain.

Examples of suitable biological samples that may be obtained from the subject which comprise cholesteryl esters (such as cholesteryl oleate) include, but are not necessarily limited to, whole blood, blood plasma, blood serum, red blood cells, cerebrospinal fluid (CSF), mucus secretions and saliva. In an embodiment, the biological sample is whole blood. In one particular embodiment, the biological sample may be blood. For example, the inventors have identified that levels of CE 18:1 in whole blood correlates to the level of CE 18:1 found in the brain, as seen in FIG. 6.

In some embodiments, the level of cholesteryl ester being determined in the subject of biological sample obtained therefrom is compared to a "reference level" of the cholesteryl ester being determined. For example, in some embodiments, the level of cholesteryl oleate in the subject or biological sample obtained therefrom is compared to a reference level of cholesteryl oleate. The reference level of cholesteryl oleate may take a variety of forms. For example, the reference level may be the level of cholesteryl oleate in a control subject or group of control subjects. The control subject may be a subject with an impaired cognitive function such as AD or dementia (impaired cognition control) or a subject without any impaired cognitive function (i.e. a healthy control). In some embodiments, the reference level can be from the same subject having their cognitive function being evaluated (i.e. at a different time point). In one embodiment, the reference level may be a calculated reference level, most preferably the average or median, for the relative or absolute amount of cholesteryl oleate of a population of individuals comprising the subject having their cognitive function evaluated. The absolute or relative amounts of cholesteryl oleate of said individuals of the population can be determined as specified elsewhere herein. It will be understood that the means of calculating a suitable reference value, preferably, the average or median, is well known to the person skilled in the art. The population of subjects referred to before shall comprise a plurality of subjects, for example, at least 5, 10, 50, 100, or 1,000 subjects.

In some embodiments, the reference level of cholesteryl oleate is a level determined from an average of subjects of similar age who do not have impaired cognitive function. For example, the reference level may be a predetermined average level of cholesteryl oleate identified from subjects who do not have impaired cognitive function, and are of similar age to the subject being evaluated. As used herein "similar age" may refer to the same age or a predetermined age bracket. For example, if the subject having their cognitive function evaluated is 73 years old, the reference level of cholesteryl oleate may be obtained as an average level obtained from subjects aged 70 to 75 years old, whom do not have impaired cognitive function. It will be understood by a person skilled in the art that other age brackets are considered appropriate. For example, the reference level may be the average percentage (%) amount of cholesteryl oleate in a blood sample taken from subjects who do not have impaired cognitive function. In this example, a subject is determined to have impaired cognitive function if the percentage (%) amount of cholesteryl oleate is less this reference level.

It will be understood that the above embodiments regarding selecting an appropriate reference level for cholesteryl oleate equally apply to selecting an appropriate reference level for cholesteryl palmitate and/or cholesteryl palmitoleate.

In one example, in some embodiments, a level of cholesteryl oleate lower than the reference level is indicative of impaired cognitive function. In one embodiment, the reference level of cholesteryl oleate may be obtained from the same subject who is having their cognitive function evaluated. For example, the level of cholesteryl oleate determined in the subject or a biological sample obtained therefrom is compared to a level of cholesteryl oleate previously obtained from the same subject, which is referred to as the reference level of cholesteryl oleate. In one embodiment, where the level of cholesteryl oleate in the subject or a biological sample obtained therefrom is lower than the reference level of cholesteryl oleate obtained from the same subject, the subject is indicated to have impaired cognitive function.

In another example, in some embodiments, a level of cholesteryl palmitate and/or cholesteryl palmitoleate higher than the reference level is indicative of impaired cognitive function. In some embodiments, where the level of cholesteryl palmitate and/or cholesteryl palmitoleate in the subject or a biological sample obtained therefrom is higher than the reference level of cholesteryl palmitate and/or cholesteryl palmitoleate obtained from the same subject, the subject is indicated to have impaired cognitive function.

In some embodiments, the level of cholesteryl ester in the subject or a biological sample obtained therefrom is monitored over time to detect changes in cognitive function. The changes in cognitive function may indicate the presence or absence of impaired cognitive function. For example, in some embodiments, the level of cholesteryl oleate may decrease over time, which may be indicative of the presence of impaired cognitive function in the subject. In an alternative embodiment, the level of cholesteryl oleate may increase over time, which may be indicative of an increase in cognitive function possibly due to the patient being treated with a suitable compound to improve cognitive function. In another example, in some embodiments, the level of cholesteryl palmitate and/or cholesteryl palmitoleate may increase over time, which may be indicative of the presence of impaired cognitive function in the subject. In an alternative embodiment, the level of cholesteryl palmitate and/or cholesteryl palmitoleate may decrease over time, which may be indicative of an increase in cognitive function possibly due to the patient being treated with a suitable compound to improve cognitive function.

In one example, the subject is determined to have impaired cognitive function if the percentage (%) amount of cholesteryl oleate is less than about 90%, 80%, 70%, 60%, 50%, 40%, 30%, 20% or 10% of the cholesteryl fatty acid esters in the sample. In another example, the subject is determined to have impaired cognitive function if the percentage (%) amount of cholesteryl oleate is less than about 70, 65%, 60%, 55%, 50%, 45%, 40%, 35% or 30% of the cholesteryl fatty acid esters in the sample. In one example, the subject is determined to have impaired cognitive function if the percentage (%) amount of cholesteryl oleate is less than about 50% of the cholesteryl fatty acid esters in the sample. For example, referring to FIG. 2, the % total of CE 18:1 in the brain in subjects with Alzheimer's disease (AD) is less than 50%.

In another example, the subject is determined to have impaired cognitive function, if the percentage (%) amount of cholesteryl palmitate and/or cholesteryl palmitoleate is greater than about 4%, 5%, 6%, 7%, 8%, 9%, 10%, 11%, 12%, 13%, 14%, or 15% of the cholesteryl fatty acid esters in the sample. In another example, the subject is determined to have impaired cognitive function, if the percentage (%) amount of cholesteryl palmitate and/or cholesteryl palmitoleate is greater than about 8%, of the cholesteryl fatty acid esters in the sample. For example, referring to FIG. 3, the % total of CE 16:0 and CE 16:1 in the brain in subjects with Alzheimer's disease (AD) is greater than 8%.

It will be understood that the % reference levels are given by way of example only.

The term "decrease" used herein generally means a decrease by a statistically significant amount. In one embodiment, the term decrease means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The term "increase" used herein generally means an increase by a staticaly significant amount. In one embodiment, the term increase means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level.

In some embodiments, the reference level for cholesteryl oleate may be the % of cholesteryl oleate in the white matter of the brains of subjects not affected by Alzheimer's disease. For example, referring to FIG. 2, the % total of CE 18:1 in the brain's white matter of subject with Alzheimer's disease (AD) is less than the % total of CE 18:1 in the brain's white matter of both healthy young and old subjects.

In some embodiments, an advantage of the present invention is that by monitoring the levels of cholesteryl ester in a subject, the subjects cognitive function can be monitored. For example, if a subject is being treated for a degenerative brain disorder, such as Alzheimer's disease or dementia, an increase in cholesteryl oleate in the subject over time is indicative of an increase in cognitive function and therefore the treatment is effective. Alternatively, if a subject is being treated for a degenerative brain disorder, such as Alzheimer's disease or dementia, a decrease in cholesteryl oleate in the subject over time is indicative of a further decline in cognitive function and therefore the treatment being administered is ineffective. In another example, if a subject is being treated for a degenerative brain disorder, such as Alzheimer's disease or dementia, a decrease in cholesteryl palmitate and/or cholesteryl palmitoleate in the subject over time is indicative of an increase in cognitive function and therefore the treatment is effective. Alternatively, if a subject is being treated for a degenerative brain disorder, such as Alzheimer's disease or dementia, an increase in cholesteryl palmitate and/or cholesteryl palmitoleate in the subject over time is indicative of a further decline in cognitive function and therefore the treatment being administered is ineffective.

In some embodiments, the period of time the level of cholesteryl oleate in the subject or a biological sample obtained therefrom is monitored is selected from about every 1 week to about every 10 years. In some embodiments, the period of time is selected from about 1 month to about 24 months (2 years). In some embodiments, the period of time is selected from about every 1 month, 3 months, 6 months, 9 months, 12 months, 15 months, 18 months, 21 months or 24 months. It will be understood by a person skilled in the art that other timeframes may be appropriate depending on the nature of the cognitive function of the subject. It will be understood that the same period of times may also apply when the level of cholesteryl palmitate and/or cholesteryl palmitoleate is being monitored.

In some aspects, the method of evaluating cognitive function in a subject may further comprise administering a treatment for impaired cognitive function. For example, the method may further comprise selecting a treatment for impaired cognitive function, wherein the treatment comprises selectively administering a composition comprising an effective amount of a therapeutic agent. In some embodiments, the treatment may comprise selectively administering a composition comprising an effective amount of an anti-dementia compound selected from the group consisting of donepezil, memantine, rivastigmine, galanthamine, and tacrine, or salts thereof, oleic acid, palm oil, cholesteryl oleate or analogue thereof, or any combinations thereof to a subject identified as having impaired cognitive function. In one embodiment, the treatment may comprise an effective amount of cholesteryl oleate or analogue thereof.

It will be understood by a person skilled in the art that cholesteryl oleate, or analogue thereof, may be administered to any subject showing signs of impaired cognitive function without having to have the subject evaluated using the method of evaluating cognitive function disclosed herein. The cholesteryl oleate may be administered in any dosage form suitable for administration to a subject, as understood by a person skilled in the art, and discussed herein.

In another aspect, the presence of beta-amyloid plaque deposits in the brain of a subject may be evaluated by determining the level of cholesteryl oleate (CE 18:1) in the brain of the subject. For example, an accumulation of beta-amyloid plaque between the nerve cells in the brain can be an indicator of Alzheimer's disease. Referring to FIGS. 12 and 13, the level of cholesteryl oleate (CE 18:1) in the brain of subjects with detectable beta-amyloid plaque in the brain (e.g. detectable by MRI) was statistically less than the level of CE 18:1 in subjects with no detectable beta-amyloid plaque in the brain. It will be appreciated that the descriptions and definitions provided relating to the method of evaluating cognitive function, and in particular the description and definitions regarding the levels of cholesteryl oleate (CE 18:1) in a subject or a biological sample obtained therefrom, also applies to the method of evaluating the presence of beta-amyloid plaque in the brain of a subject, and shall be taken to apply mutatis mutandis to the method of evaluating the presence of beta-amyloid plaque in the brain of a subject.

Methods of Determining the Level of Cholesteryl Ester

The level of cholesteryl ester in the subject or biological sample obtained therefrom may be determined using any technique known to the person skilled in the art. For example, suitable techniques used to determine the level of cholesteryl oleate include, but are not limited to, liquid chromatography/mass spectroscopy (LC/MS), gas chromatography-mass spectroscopy (GC/MS), mass spectroscopy (MS), liquid chromatography (LC), gas chromatography (GC), immunoblotting, ELISA assays, and protein microarrays, or combinations thereof. In some embodiments, the level of cholesteryl oleate is determined using liquid chromatography/mass spectrometry (LC/MS) analysis.

The sample may be sent to a commercial laboratory for measurement or the use of commercially available assay kits. Exemplary kits and suppliers will be apparent to the skilled artisan. In various embodiments, the cholesteryl oleate may be determined, detected and/or quantified using lateral flow devices, such as for point-of-care use, as well as spot check colorimetric tests.

The person skilled in the art would understand that the above mention techniques are also suitable for determining the levels cholesteryl palmitate and/or cholesteryl palmitoleate in the subject or biological sample obtained therefrom.

Kits

In another embodiment, a kit may be provided for evaluating cognitive function in a subject. The kits may include reagents suitable for determining levels of cholesteryl oleate in a sample obtained from a subject. Optionally, the kits may contain one or more control samples or references. Typically, a comparison between the levels of cholesteryl ester in the subject and level of the cholesteryl ester in the control sample is indicative of the subject's cognitive function. In some embodiments, the level of cholesteryl oleate in the subject being less than or equal to the level of cholesteryl oleate in the control sample is indicative of the likelihood of impaired cognitive function. In other embodiments, the level of cholesteryl palmitate and/or cholesteryl palmitoleate in the subject being greater than or equal to the level of cholesteryl palmitate and/or cholesteryl palmitoleate in the control sample is indicative of the likelihood of impaired cognitive function.

In some embodiments, the kit may also include written information providing a reference level to compare the cholesteryl ester (i.e. cholesteryl oleate) level in the subject to (e.g., predetermined values).

Cholesteryl Oleate (CE 18:1), Cholesteryl Palmitate (CE 16:0) and Cholesteryl Palmitoleate (CE 16:1)

Cholesteryl esters are largely synthesized in the body by the transfer of fatty acids to cholesterol from either phosphatidyl choline (PC) or acyl-CoA, depending on where the reaction is taking place. For example, in the plasma/peripheral tissues, the reaction is catalysed by either lecithin cholesterol acyl transferase (LCAT). Alternatively, in the lumen, the reaction is catalysed by acyl-coenzyme A (ACAT1). The general structure for a cholesteryl ester is provided below:

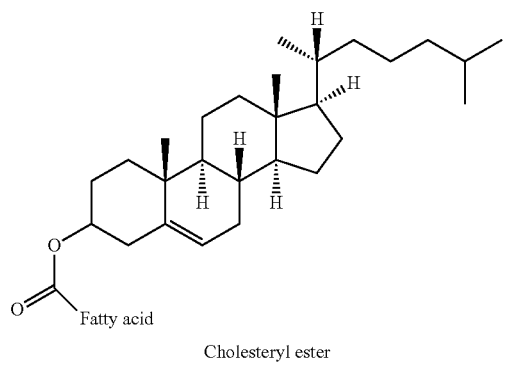
Cholesteryl ester

The ester bond is formed via esterification between the carboxylate group (—COOH) group of the fatty acid and the hydroxyl group (—OH) of the cholesterol. Cholesteryl esters, and their analogues thereof, are typically defined by the length and saturation of the fatty acid conjugated to the cholesterol, i.e. cholesteryl oleate (CE 18:1), which indicates that the fatty acid conjugated to the cholesterol is 18 carbons long, with one C=C double bond. For example, cholesteryl oleate (CE 18:1) is a fatty acid ester of cholesterol, and is formed by the esterification of cholesterol with oleic acid, and the general structure is provided below:

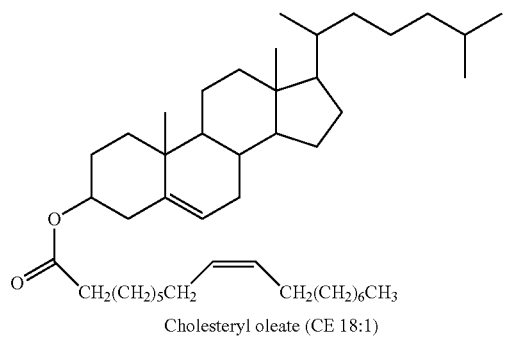
Cholesteryl oleate (CE 18:1)

It will be understood by the person skilled in the art, that the structure for cholesteryl oleate may also be represented as follows:

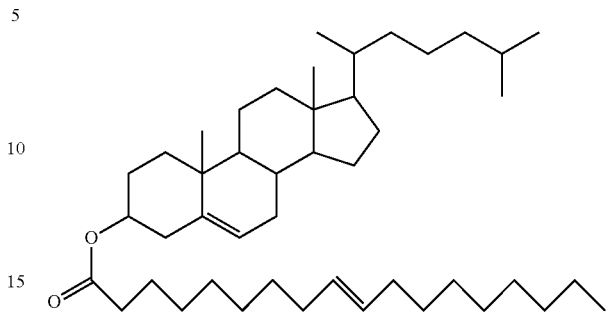

In another example, cholesteryl palmitate (CE 16:0) is a fatty acid ester of cholesterol, and is formed by the esterification of cholesterol with palmitic acid, and the general structure is provided below:

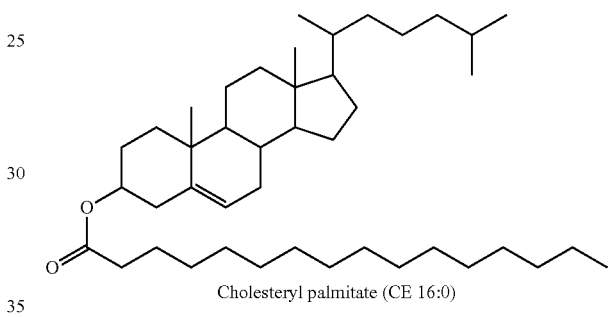
Cholesteryl palmitate (CE 16:0)

where the (16:0) indicates the fatty acid is 16 carbon atoms long, with no —C=C-double bonds present.

In another example, cholesteryl palmitoleate (CE 16:1) is a fatty acid ester of cholesterol, and is formed by the esterification of cholesterol with palmitoleic acid, and the general structure is provided below:

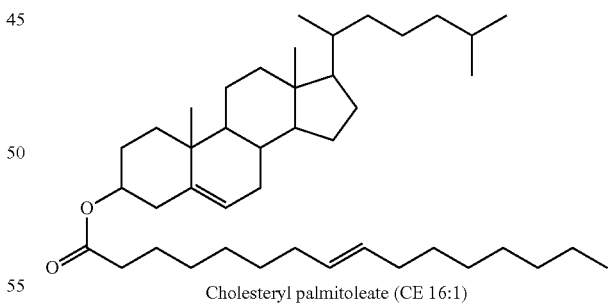
Cholesteryl palmitoleate (CE 16:1)

where the (16:1) indicates the fatty acid is 16 carbon atoms long, with a one —C=C— double bond present.

Methods of Improving Cognitive Function in a Subject

The present inventors have identified that the level of cholesteryl oleate in the human brain of a subject suffering from impaired cognitive function, such as seen in Alzheimer's disease, is lower compared to subjects that do not have any impaired cognitive function. Accordingly, the present inventors have surprisingly identified that treating a subject with impaired cognitive function, such as Alzheimer's disease, with an effective amount of cholesteryl oleate or an analogue or a derivative thereof, may improve the cognitive function in the subject. Without wishing to be bound by theory, the present inventors believe that treating a subject with impaired cognitive function, such as Alzheimer's disease, with an effective amount of cholesteryl oleate, or an analogue thereof, may also increase the level of cholesteryl oleate in the brain. The present inventors have also been identified that a diet enriched with oleic acid may also increase the level of cholesteryl oleate in the brain.

Accordingly, in one embodiment, there is provided a method of improving cognitive function in a subject, the method comprising administering to the subject an effective amount of cholesteryl oleate, or an analogue thereof according to Formula 1:

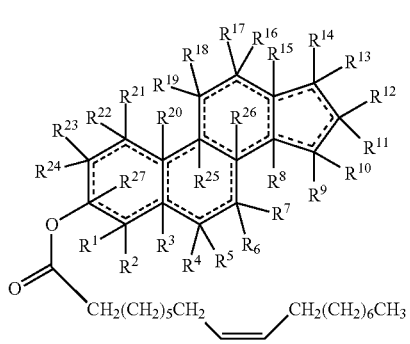

Formula 1 or a conjugate, salt or prodrug thereof,
wherein
══════ represents a single or double bond; and
$R^1$ to $R^{27}$ are each either absent or independently selected from the group consisting of hydrogen, alkyl and alkenyl, wherein each alkyl and alkenyl is optionally substituted with one or more alkyl which may be further optionally substituted.

In some embodiments, $R^1$ to $R^{27}$ are each either absent or independently selected from the group consisting of hydrogen, $C_{1-12}$alkyl, and $C_{2-12}$alkenyl, wherein each $C_{1-12}$alkyl and $C_{2-12}$alkenyl is optionally substituted with the one or more $C_{1-12}$alkyl. In some embodiments, $R^1$ to $R^{27}$ are each either absent or independently selected from the group consisting of hydrogen, $C_{1-12}$alkyl, and $C_{2-8}$alkenyl wherein each $C_{1-12}$alkyl and $C_{2-8}$alkenyl is optionally substituted with the one or more $C_{1-8}$alkyl. In some embodiments, $R^1$ to $R^{27}$ are each either absent or independently selected from the group consisting of hydrogen, $C_{1-6}$ alkyl, and $C_{2-6}$alkenyl, wherein each $C_{1-6}$alkyl and $C_{2-6}$alkenyl is optionally substituted with the one or more $C_{1-6}$alkyl. In some embodiments, $R^1$ to $R^{27}$ are each either absent or independently selected from the group consisting of hydrogen, $C_{1-4}$ alkyl, and $C_{2-4}$alkenyl, wherein each $C_{1-4}$alkyl and $C_{2-4}$alkenyl is optionally substituted with the one or more $C_{1-4}$alkyl. In one embodiment, $R^1$ to $R^{13}$ and $R^1$ to $R^{27}$ are each either absent or independently hydrogen or $C_{1-12}$alkyl, and $R^{14}$ is either absent or $C_{1-12}$alkyl or $C_{2-12}$alkenyl, wherein each $C_{1-12}$alkyl and $C_{2-12}$alkenyl is optionally substituted with the one or more $C_{1-12}$alkyl.

In some embodiments, the cholesteryl oleate, or analogue thereof, according to Formula 1 that is administered to a subject, has the following structure Formula 1a:

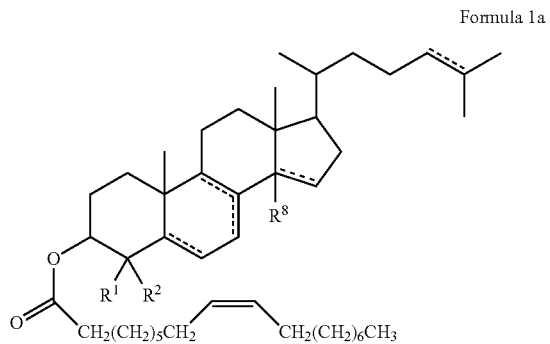

Formula 1a or a conjugate, salt or prodrug thereof,
wherein
══════ represents a single or double bond;
$R^1$ and $R^2$ are each independently hydrogen or $C_{1-12}$alkyl; and
$R^8$ is either absent or hydrogen or $C_{1-12}$alkyl.

In some embodiments, $R^1$ and $R^2$ are each independently hydrogen or $C_{1-6}$alkyl, and $R^8$ is either absent or hydrogen or $C_{1-6}$alkyl. In some embodiments, $R^1$ and $R^2$ are each independently hydrogen or methyl, and $R^8$ is either absent or hydrogen or methyl.

In some embodiments, $R^1$ and $R^2$ are each independently selected from the group consisting of hydrogen, $C_{1-12}$alkyl, $C_{1-10}$alkyl, $C_{1-8}$alkyl, $C_{1-6}$alkyl, $C_{1-4}$alkyl and $C_{1-2}$alkyl, and $R^8$ is either absent or selected from the group consisting of hydrogen, $C_{1-12}$alkyl, $C_{1-10}$alkyl, $C_{1-8}$alkyl, $C_{1-6}$alkyl, $C_{1-4}$alkyl and $C_{1-2}$alkyl. In one embodiment, $R^1$ and $R^2$ are each independently selected from hydrogen or methyl, and $R^8$ is either absent or hydrogen or methyl.

In some embodiments, the cholesteryl oleate, or analogue thereof according to Formula 1a has the following structure:

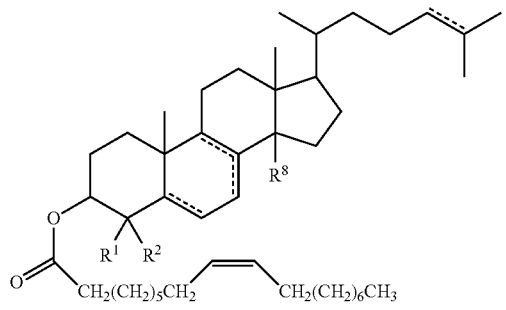

or a conjugate, salt or prodrug thereof,
wherein
══════ represents a single or double bond; and
$R^1$, $R^2$, and $R^8$ are each independently hydrogen or methyl.

In some embodiments, the cholesteryl oleate analogue according to Formula 1a is selected from cholesterol analogues that are naturally present in the lanosterol to cholesterol biosynthesis pathway, which would be understood by the person skilled in the art. For example, the cholesteryl oleate, or analogue thereof according to Formula 1a may be selected from the group consisting of lanosteryl oleate, dihydrolanosteryl oleate, zymosteryl oleate, zymostenyl oleate, lathosteryl oleate, 7-dehydrodesmosteryl oleate, 7-dehydrocholesteryl oleate, 8-dehydrocholesteryl oleate, desmosteryl oleate and cholesteryl oleate, the structures of which are provided as follows:

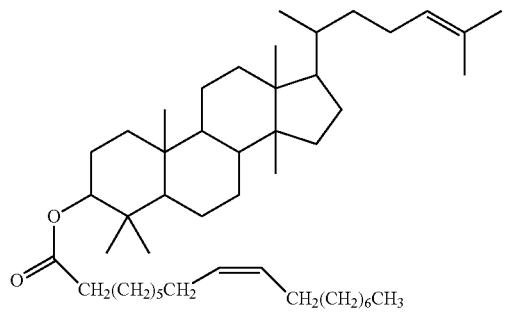

lanosteryl oleate

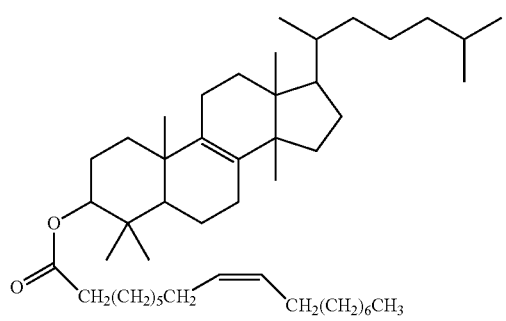

dihydrolanosteryl oleate

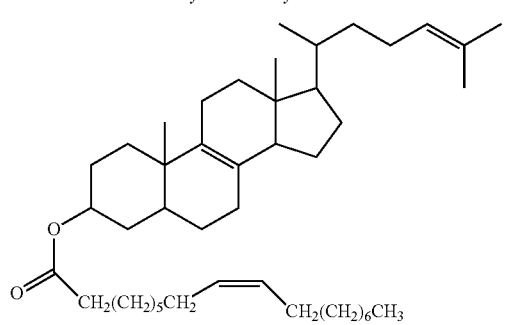

zymosteryl oleate

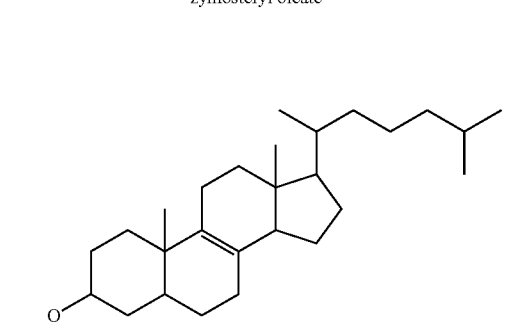

zymostenyl oleate

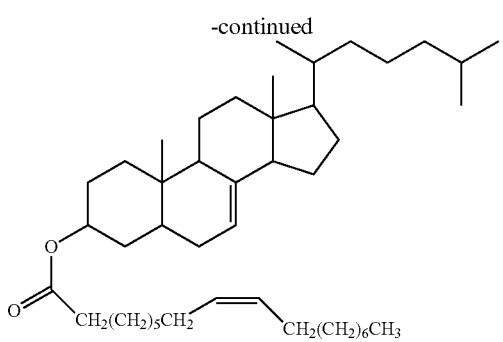

lathosteryl oleate

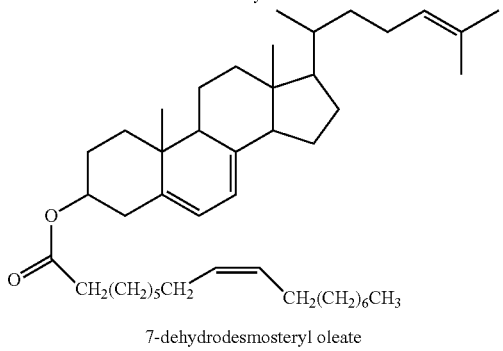

7-dehydrodesmosteryl oleate

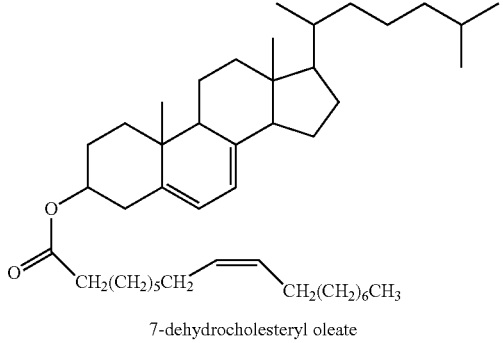

7-dehydrocholesteryl oleate

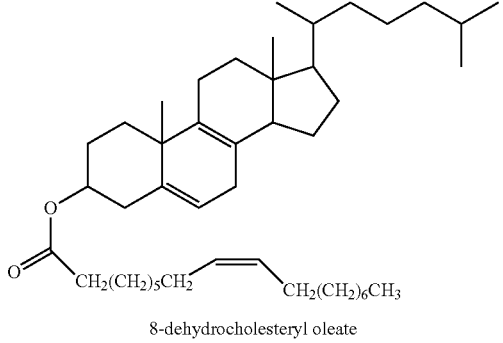

8-dehydrocholesteryl oleate

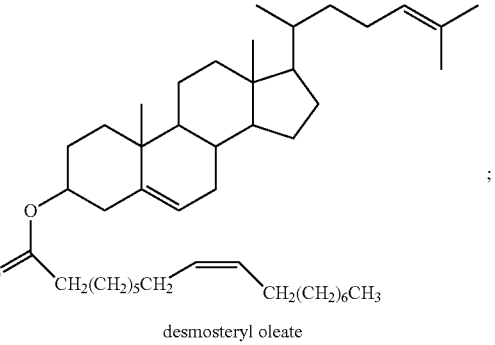

desmosteryl oleate

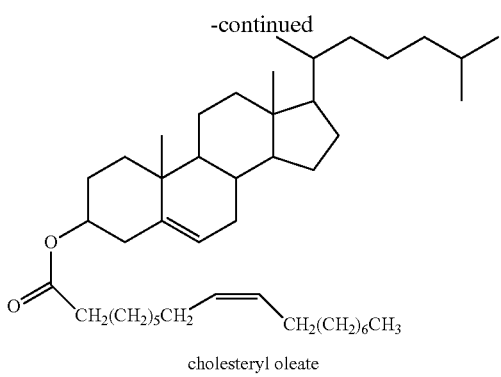
cholesteryl oleate or a conjugate, salt or prodrug thereof.

In one embodiment, there is provided a method of improving cognitive function in a subject, the method comprising administering to the subject an effective amount of cholesteryl oleate, which has the following structure:

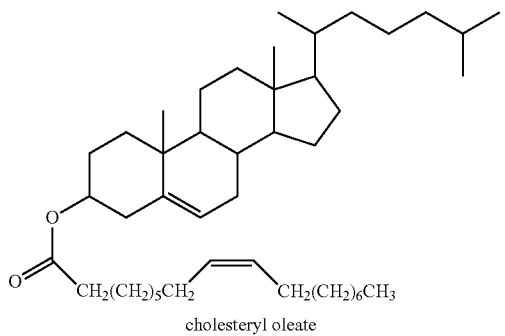
cholesteryl oleate or a conjugate, salt or prodrug thereof.

It will be understood that the structure of cholesteryl oleate, or analogues thereof, disclosed herein are not to be limited to a particular stereochemistry (such as E/Z configuration, cis-/trans-isomerisation), and unless specified, the person skilled in the art would understand that the structures are not intended to be limited as such.

In one embodiment, the structure of cholesteryl oleate is as follows:

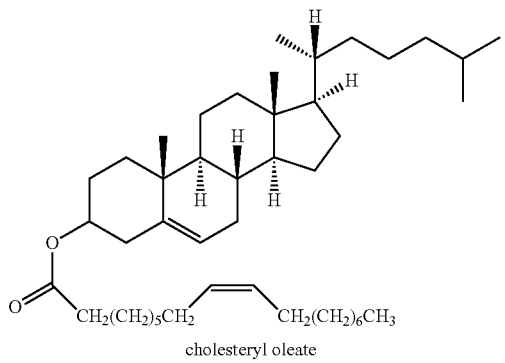
cholesteryl oleate

It again will be understood by a person skilled in the art that cholesteryl oleate or analogue thereof, may be administered to any subject showing signs of impaired cognitive function without having to have the subject evaluated using the method of evaluating cognitive function disclosed herein. The cholesteryl oleate, or analogue thereof, may be administered in any dosage form suitable for administration to a subject, as understood by a person skilled in the art, and discussed herein.

In some embodiments, administering cholesteryl oleate to a subject may increase the subjects cognitive function. For example, referring to FIG. 11, subjects fed with an cholesteryl oleate (CE 18:1) oral administration spent more time investigating the target zone of a Barnes maze during the probe trial where the escape hutch used to be located, indicating an increase in memory.

In some embodiments, the cholesteryl oleate, or analogue thereof, is the only therapeutically effective ingredient administered to the patient. In other embodiments, the cholesteryl oleate or analogue thereof is the only cognitive enhancing therapeutically effective ingredient administered to the patient. By way of example, in some embodiments, the cholesteryl oleate or analogue thereof is not administered to the subject with other additional cognitive enhancing therapeutic ingredients.

The cholesteryl oleate or analogue thereof as described herein may also be used for the manufacture of a medicament or nutraceutical for improving cognitive function in a subject.

In another embodiment, there is provided a method of improving cognitive function in a subject, the method comprising administering to the subject an effective amount oleic acid. For example, the subject could be administered with an effective amount of palm oil, which comprises a high level of oleic acid. For example, it has been identified that a diet enriched with oleic acid may increase the subjects cognitive function (see FIGS. 8 and 9). It has also been identified that a diet enriched with oleic acid may also increase the levels of cholesteryl oleate in a subject compared to diets absent of oleic acid or enriched with other fatty acids other than oleic acid (see FIG. 7).

In another embodiment, there is provided a method of identifying a therapeutically effective compound for improving cognitive function in a subject, comprising administering an amount of a cholesteryl ester, or an analogue thereof, to an animal to determine if the animal has improved cognitive function. The cholesteryl ester, or analogue thereof, may be selected from any one of the cholesteryl ester compounds defined herein, including for example, a cholesteryl ester, or an analogue thereof, according to Formula 1 and Formula 1a, including cholesteryl oleate, or an analogue thereof, as defined herein.

Pharmaceutical and Nutraceutical Compositions

In some embodiments, the cholesteryl oleate or analogue thereof described herein is administered with a pharmaceutically acceptable carrier or excipient to the subject in the form of a pharmaceutical composition/formulation. As used herein, the term "pharmaceutically acceptable carrier" or "pharmaceutically acceptable excipient" includes any and all solids or solvents (such as phosphate buffered saline buffers, water, saline) dispersion media, coatings, isotonic and absorption delaying agents, and the like, compatible with pharmaceutical administration. The pharmaceutically acceptable carriers or excipients must be 'acceptable' in the sense of being compatible with the other ingredients of the composition and not deleterious to the recipient thereof. The pharmaceutical carrier or excipient can be either solid or liquid. Solid form preparations include, for example, powders, tablets, dispersible granules, capsules (e.g. enteric formulation/dosage form), cachets, and suppositories. A solid carrier or excipient can be one or more substances that can also act as diluents, flavoring agents, solubilizers, lubricants, suspending agents, binders, or tablet disintegrating agents; it can also be an encapsulating material. In powders, the carrier or excipient is generally a finely divided solid that is in a mixture with the finely divided active component. In tablets, the cholesteryl oleate or analogue thereof is mixed with the carrier or excipient having the necessary binding properties in suitable proportions and compacted in the shape and size desired.

The amount of pharmaceutically acceptable carrier or excipient will depend upon the level of the compound and any other optional ingredients that a person skilled in the art would classify as distinct from the carrier or excipient (e.g., other active agents). The formulations of the present invention may comprise, for example, from about 5% to 99.99%, or 25% to about 99.9% or from 30% to 90% by weight of the composition, of a pharmaceutically acceptable carrier or excipient. The pharmaceutically acceptable carrier or excipient can, in the absence of other adjuncts, form the balance of the composition. In one embodiment, the pharmaceutically acceptable carrier or excipient may form the balance of the composition with cholesteryl oleate or an analogue thereof (i.e. the pharmaceutical composition consists of cholesteryl oleate, or an analogue thereof, and a pharmaceutically acceptable carrier or excipient).

In some embodiments, the pharmaceutical composition comprises cholesteryl oleate, or an analogue thereof, as the only therapeutically active ingredient. In other embodiments, the pharmaceutical composition comprises cholesteryl oleate, or an analogue thereof, as the only cognitive enhancing therapeutically active ingredient. With regard to this embodiment, it will be understood that other non-cognitive enhancing therapeutically active ingredients may be included in the composition along with cholesteryl oleate, or an analogue thereof.

Optionally, the pharmaceutical composition of the present disclosure further comprises other additional components, for example therapeutic and/or prophylactic ingredients. The invention thus relates in a further aspect to pharmaceutical composition comprising a cholesteryl oleate or analogue thereof, one or more pharmaceutically acceptable carriers or excipients together with one or more other active agents. Generally, the amount of other active agent present in the pharmaceutical composition is sufficient to provide an additional benefit either alone or in combination with the other ingredients in the composition.

It will be understood by the person skilled in the art that these optional components may be categorized by their therapeutic or aesthetic benefit or their postulated mode of action. However, it is also understood that these optional components may, in some instances, provide more than one therapeutic or aesthetic benefit or operate via more than one mode of action. Therefore, classifications herein are made for the sake of convenience and are not intended to limit the component to that particular application or applications listed. Also, when applicable, the salts of the components are useful herein.

When other active agents (such as compounds which also improve cognitive function, such as anti-Alzheimer's disease or anti-dementia compounds, or other compounds which do not improve cognitive function, but may alleviate other conditions (e.g. pain) are present in the pharmaceutical formulation of the present invention, the dose of the compound may either be the same as or differ from that employed when the other additional components are not present. Appropriate doses will be readily appreciated by those skilled in the art.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized moulds and allowed to cool and solidify.

Powders and tablets may contain between about 5% to about 70% by weight of cholesteryl oleate or analogue thereof. Suitable carriers or excipients include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the cholesteryl oleate or analogue thereof with encapsulating material as a carrier providing a capsule in which the inhibitor (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid compositions comprising cholesteryl oleate or analogues thereof may include, for example, solutions suitable for oral or parenteral administration, suspensions, and emulsions suitable for oral administration. Sterile water solutions of the cholesteryl oleate or analogue thereof or sterile solutions of the cholesteryl oleate or analogue thereof in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the cholesteryl oleate or analogue thereof in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, for example from 5 to 9, or from 7 to 8.

Single or multiple administrations of the cholesteryl oleate or analogue thereof can be carried out with dose levels and pattern being selected by the treating practitioner or the patient as instructed. In any event, the pharmaceutical formulations should provide a quantity of cholesteryl oleate or analogue thereof sufficient to effectively improve cognitive function.

When used for pharmaceutical purposes, the cholesteryl oleate or analogue thereof may be generally formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan.

The compositions can additionally include a stabilizer, enhancer or other pharmaceutically acceptable carriers, excipients or vehicles. A pharmaceutically acceptable carrier or excipient can contain a physiologically acceptable compound that acts, for example, to stabilize the compounds. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. Examples of carriers, excipients, stabilizers or adjuvants can be found in Remington's Pharmaceutical Sciences, Mack Publishing Company, Philadelphia, Pa., 17th ed. (1985).

The pharmaceutical formulations or compositions containing cholesteryl oleate or analogue thereof may be delivered to any tissue or organ using any delivery method known to the ordinarily skilled artisan. They may be formulated for parenteral administration (subcutaneously, intramuscularly, intravenously), or for oral ingestion, inhalation, sublingual or topical application. They may also be formulated to be administered enterally, rectally, vaginally, or by another appropriate route.

Effective dosage of the formulations will vary depending on many different factors, including means of administration, target site, physiological state of the patient, and other medicines administered. Thus, treatment dosages will need to be titrated to optimize safety and efficacy. In determining the effective amount of a compound to be administered, the physician should evaluate the particular compound being used, the degenerative brain disorder being treated; the age, weight, and overall condition of the patient, circulating plasma levels, vector toxicities, progression of the disease, and the production of anti-vector antibodies. The size of the dose also will be determined by the existence, nature, and extent of any adverse side-effects that accompany the administration of a particular vector.

The carriers or excipients must be pharmaceutically acceptable in the sense of being compatible with the other ingredients, such as sugars, hydroxyethylstarch (HES), dextrates (e.g., cyclodextrins, such as 2-hydroxypropyl-β-cyclodextrin and sulfobutylether-β-cyclodextrin), polyethylene glycols, and pectin. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions are listed in "Remington: The Science & Practice of Pharmacy", 19.sup.th ed., Williams & Williams, (1995), and in the "Physician's Desk Reference", 52.sup.nd ed., Medical Economics, Montvale, N.J. (1998), and in "Handbook of Pharmaceutical Excipients", Third Ed., Ed. A. H. Kibbe, Pharmaceutical Press, 2000.

In some embodiments, the cholesteryl oleate, or analogue thereof, is provided as a nutraceutical composition. As used herein, the term "nutraceutical" is commonly understood to mean any substance containing cholesteryl oleate, or analogue thereof, that is a food or liquid, part of a food or liquid, or is an addition to food or liquid, and that provides an improvement of cognitive function in a subject, Such products may range from isolated nutrients, dietary supplements, specific diets, genetically engineered designer foods, herbal products, and processed foods such as cereals, soups, nutritional bars, beverages, tablets, lozenges, wafers, capsules, solutions, emulsions, bars, gels, shakes, yogurts, breads, juices, caplets, gels, jellies, serums, powders, sprays (i.e. nasal sprays, mouth sprays), liquids and other suitable forms.

In some embodiments, the nutraceutical compositions may be provided in the form of a liquid, a powder, a solid, a semi-solid, or a semi-liquid. For example, a nutraceutical composition is a composition that is edible and includes additional nutrients along with the cholesteryl oleate, or analogue thereof.

The nutraceutical composition may comprise cholesteryl oleate, or an analogue thereof, and a nutraceutically acceptable excipient. The nutraceutically acceptable excipient may be selected from one or more of the excipients described above as a pharmaceutically acceptable excipient, and is understood to be an excipient suitable for consumption.

Cholesteryl Oleate and Dosage Amounts

In some embodiments, the pharmaceutical or nutraceutical composition comprises a therapeutically effective amount of cholesteryl oleate or analogue thereof. The content of the cholesteryl oleate or analogue thereof in the pharmaceutical or nutraceutical composition is, for example, from about 0.1% to about 100% w/w of the composition. For example, the cholesteryl oleate or analogue thereof may be administered to the subject as pure cholesteryl oleate (i.e. 100% w/w). In other embodiments, the cholesteryl oleate or analogue thereof may be administered with a pharmaceutically or nutraceutically acceptable excipient.

In some embodiments, the concentration of the cholesteryl oleate or analogue thereof, in the pharmaceutical or nutraceutical composition may be greater than about 0.1%, 1%, 5%, 10%, 20%, 30%, 40%, 50%, 60%, 70%, 80%, or 90% w/w of the composition. For example, the content of the cholesteryl oleate or analogue thereof in the pharmaceutical or nutraceutical composition may at least about 0.1%, 1%, 2%, 3%, 4%, 5%, 10%, 20%, 50%, 60%, 70%, 80% or 90% w/w of the composition. In some embodiments, the concentration of the cholesteryl oleate or analogue thereof, in the pharmaceutical or nutraceutical composition may be about 0.1% to 100%, 5% to 95%, 10% to 90%, 15% to 85%, 20% to 80%, 25% to 75%, 30% to 70%, 35% to 65% or 40% to 60% w/w. In some embodiments, the concentration of the cholesteryl oleate or analogue thereof, in the pharmaceutical or nutraceutical composition may less than about 90%, 80%, 70%, 60%, 50%, 40%, 30%, 20%, 10% or 5% w/w. It will be appreciated that any one or more of these % w/w values may be combined to form a suitable range (for example the concentration of the cholesteryl oleate or analogue thereof, in the pharmaceutical or nutraceutical composition may be from about 5% to about 50% w/w).

In some embodiments, the pharmaceutical or nutraceutical composition may comprise cholesteryl oleate, or an analogue thereof, as the only therapeutically active ingredient or the only cognitive enhancing therapeutically active ingredient, with the remaining ingredients selected from an appropriate pharmaceutically or nutraceutically acceptable excipient or ingredient to form the composition. By way of example only, the nutraceutical may be a jelly, wherein the jelly comprises agar, flavouring agents, sodium hydroxide, water and cholesteryl oleate, or an analogue thereof. With reference to this non-limiting example, the cholesteryl oleate, or analogue thereof, may be provided in the nutraceutical jelly in an amount of from about 1% to about 90%, for example of about 1%, 5%, 10%, 15%, 20%, 25%, 30%, 35%, 40%, 45%, 50%, 55%, 60%, 65%, or 70% w/w of the jelly, wherein the remaining % w/w amount are selected from nutraceutically acceptable ingredients suitable to form the jelly. In some embodiments, it will be appreciated that the pharmaceutical or nutraceutical composition may be selected from any suitable dosage form, food or liquid dietary product and still comprise cholesteryl oleate, or an analogue thereof, as the only therapeutically active ingredient effective. By way of another example, the nutraceutical may be a liquid (e.g. a juice), wherein the liquid contains cholesteryl oleate, or an analogue thereof, and one or more suitable ingredients to form the liquid component.

It will be appreciated that the pharmaceutical or nutraceutical composition may comprise a cognitive function improving amount of cholesteryl oleate, or an analogue thereof. For example, the cholesteryl oleate, or an analogue thereof, is provided in the nutraceutical composition in an amount effective to improve cognitive function. As such, it will be appreciated that the cholesteryl oleate is a therapeutically active ingredient and not a non-active ingredient, carrier or excipient.

In some embodiments, the cholesteryl oleate, or analogue thereof, is administered to the subject in the form of high-density lipoprotein (HDL) cholesterol. It will be understood by the person skilled in the art that the cholesteryl oleate, or analogue thereof, may be bound within the HDL, and administered to the subject. Upon administration, the cholesteryl oleate is released from the HDL. In some embodiments, the cholesteryl oleate, or analogue thereof, may be administered to the subject in the form of high-density lipoprotein (HDL) cholesterol as a nutraceutical as defined above, or combined with a pharmaceutically acceptable carrier or excipient as defined above.

The amount of cholesteryl oleate, or an analogue thereof, present in the pharmaceutical or nutraceutical compositions may be present in an amount so as to deliver from about 1 mg to 100 g of cholesteryl oleate, or an analogue thereof, to the subject. For example, the pharmaceutical or nutraceutical composition may deliver at least about 1 mg, 5 mg, 10 mg, 20 mg, 50 mg, 100 mg, 150 mg, 200 mg, 500 mg, 750 mg, 1 g, 5 g, 10 g, 50 g or 100 g of cholesteryl oleate, or an analogue thereof, to the subject. In one embodiment, the compositions may deliver from about 10 mg to 50 g, 50 mg to 10 g, or 100 mg to 1 g of cholesteryl oleate, or an analogue thereof, to the subject. In some embodiments, the pharmaceutical or nutraceutical composition may deliver about 1 mg, 5 mg, 10 mg, 20 mg, 30 mg, 40 mg, 50 mg, 100 mg, 150 mg, 200 mg, 500 mg, 750 mg, 1 g, 5 g, 10 g, 50 g or 100 g of cholesteryl oleate, or an analogue thereof, to the subject. In some embodiments, the pharmaceutical or nutraceutical composition may deliver less than about 100 g, 50 g, 10 g, 5 g, 1 g, 750 mg, 500 mg, 200 mg, 150 mg, 100 mg, 50 mg, 40 mg, 30 mg, 20 mg, 10 mg, or 5 mg of cholesteryl oleate, or an analogue thereof, to the subject. It will be appreciated that any one or more of these mg values may be combined to form a suitable range (for example the pharmaceutical or nutraceutical composition may deliver from about 5 mg to about 500 mg of cholesteryl oleate, or an analogue thereof, to the subject).

The amount of cholesteryl oleate, or analogue thereof, present in the pharmaceutical or nutraceutical compositions may be present in an amount so as to deliver from about 1 mg to 100 g of cholesteryl oleate when administered once a day to the subject. In one embodiment, the compositions may deliver about 1 mg of cholesteryl oleate when administered once a day. In one embodiment, the compositions may deliver from about 10 mg to 50 g of cholesteryl oleate, or analogue thereof, when administered once a day to the subject. In a further embodiment, the compositions may deliver an amount selected from the group consisting of 20 mg to 25 g, 50 mg to 15 g, 100 mg to 10 g, or 500 mg to 1 g of cholesteryl oleate, or analogue thereof, when administered once a day to the subject. In some embodiments, the compositions may deliver at least about 1 mg, 10 mg, 20 mg, 50 mg, 100 mg, 200 mg, 300 mg, 400 mg, 500 mg, 750 mg, 1 g, 5 g, 10 g, 25 g or 50 g of cholesteryl oleate, or analogue thereof, when administered once a day to the subject. In other embodiments, the compositions may deliver less than about 50 g, 25 g, 10 g, 5 g, 1 g, 750 mg, 500 mg, 400 mg, 300 mg, 200 mg, 100 mg, 50 mg, 20 mg, 10 mg or 5 mg of cholesteryl oleate, or analogue thereof, when administered once a day to the subject. It will be appreciated that any one or more of these values may be combined to form a suitable range (for example the compositions may deliver from about 100 mg to about 750 mg of cholesteryl oleate, or analogue thereof, when administered once a day to the subject).

In some embodiments, the pharmaceutical or nutraceutical compositions may be administered to the subject in two servings per day; wherein the compositions may be prepared to deliver from about 0.5 mg to 50 g, 5 mg to 25 g, 10 mg to 12.5 g, 25 mg to 7.5 g, 50 mg to 6.25 g, or 250 mg to 5 g of cholesteryl oleate, or analogue thereof, per serving when administered twice daily to the subject. In other embodiments, the formulation or nutritional composition may be administered to the subject according to a regimen that is other than two times a day, e.g., one time a day, three times a day, four times a day, etc.; it should be understood that the particular amount of cholesteryl oleate, or analogue thereof, contained within a serving of the formulation or nutritional composition can be adjusted to account for the administration regimen so that the subject is administered the desired total amount of cholesteryl oleate, or analogue thereof, per day, as described above.

In further embodiments, the administration of cholesteryl oleate, or analogue thereof, or a pharmaceutical or nutraceutical comprising cholesteryl oleate, or analogue thereof, to a subject may occur at regular intervals includes daily administration or weekly administration. In further embodiments, the term refers to administration 1-2 times per week, administration 1-3 times per week, administration 2-3 times per week, administration 1-4 times per week, administration 1-5 times per week, administration 2-5 times per week, administration 3-5 times per week, administration 1-2 times per day, administration 1-3 times per day, administration 1-4 times per day, administration 2-3 times per day, administration 2-4 times per day, administration 3-4 times per day, administration 2-5 times per day, administration 3-5 times per day, or administration 4-5 times per day.

In some embodiments, the dosages of cholesteryl oleate, or analogue thereof, may also generally range between about 0.1 mg and about 2 g per kilogram of body weight, for example between about 0.2 mg and about 1 g per kg of body weight. For example, the dosage of cholesteryl oleate, or analogue thereof, may be about 0.1 mg to 2 g, 1 mg, to 1.7 g, 5 mg to 1.5 g, 10 mg to 1.2 mg, 50 mg to 1 g, 100 mg to 900 mg, 200 mg to 800 mg, 300 mg to 700 mg, or 400 to 600 mg per kg of body weight. In some embodiments, the dosage of cholesteryl oleate, or analogue thereof, may be at least about 0.1 mg, 1 mg, 5 mg, 10, mg, 20 mg, 50 mg, 100 mg, 200 mg, 400 mg, 500 mg, 700 mg, or 1 g per kg of body weight. In some embodiments, the dosage of cholesteryl oleate, or analogue thereof, may be at least about 50 mg, 100 mg, 150 mg, 200 mg, 250 mg, 300 mg, 350 mg, 400 mg, 450 mg, or 500 mg per kg of body weight. In some embodiments, the dosage of cholesteryl oleate, or analogue thereof, may be greater than about 50 mg, 100 mg, 150 mg, 200 mg, 250 mg, 300 mg, 350 mg, 400 mg, 450 mg, or 500 mg per kg of body weight. In some embodiments, the dosage of cholesteryl oleate, or analogue thereof, may be about 400 mg, 410 mg, 420 mg, 430 mg, 440 mg, 450 mg, 460 mg, 470 mg, 480 mg, 490 mg, or 500 mg. In some embodiments, the dosage of cholesteryl oleate, or analogue thereof, may be less than about 1 g, 700 mg, 500 mg, 400 mg, 200 mg, 100 mg, 50 mg, 20 mg, 10 mg, 5 mg, or 1 mg per kg of body weight. It will be appreciated that any one or more of these dosage rates may be combined to form a suitable range (for example the dosage of cholesteryl oleate, or analogue thereof, may be from about 20 mg to about 700 mg per kg of body weight). As seen in FIG. 11, a dosage rate of 470 mg of cholesteryl oleate per kg of bodyweight can lead to improved cognitive function in mice.

It will be appreciated that dosage amounts and regimens of the cholesteryl oleate, or an analogue thereof, described herein are applicable to both the method of improving cognitive function and the pharmaceutical/nutraceutical compositions as described herein, and not limited to any one embodiment or aspect of the present disclosure.

In one embodiment, the method of improving cognitive function comprises administering cholesteryl oleate, or an analogue thereof, as the only therapeutically active ingredient. In another embodiment, the method of improving cognitive function comprises administering cholesteryl oleate, or an analogue thereof, as the only cognitive enhancing therapeutically active ingredient. For example, in some embodiments, where the cholesteryl oleate, or an analogue thereof, is the only cognitive enhancing therapeutically active ingredient being administered, it will be understood that no additional cognitive enhancing therapeutically active ingredient is administered.

In one embodiment, the pharmaceutical or nutraceutical composition comprises cholesteryl oleate, or an analogue thereof, as the only therapeutically active ingredient. In one embodiment, the pharmaceutical or nutraceutical composition comprises cholesteryl oleate, or an analogue thereof, as the only cognitive enhancing therapeutically active ingredient. For example, in some embodiments, where the compositions comprise cholesteryl oleate, or an analogue thereof, as the only cognitive enhancing therapeutically active ingredient, it will be understood that the compositions do not comprise any additional cognitive enhancing therapeutically active ingredient.

In one embodiment, the method of improving cognitive function does not comprise the administration of a liposomal composition or a complex selected from micelles, vesicles or emulsions. In one embodiment, the pharmaceutical or nutraceutical composition is not a liposomal composition. or a complex selected from micelles, vesicles or emulsions.

In one embodiment, the cholesteryl oleate, or an analogue thereof, used in the method of improving cognitive function and/or used in the pharmaceutical or nutraceutical composition is not incorporated into liposomes, emulsions, micelles and/or vesicles.

In one embodiment, the method of improving cognitive function does not comprise the administration of a guggelsterol or a guggelsterone. In one embodiment, the pharmaceutical or nutraceutical composition does not comprise a guggelsterol or a guggelsterone.

In one embodiment, the method of improving cognitive function does not comprise the administration of an anticancer drug. In one embodiment, the pharmaceutical or nutraceutical composition does not comprise an anticancer drug.

In one embodiment, the method of improving cognitive function does not comprise the administration of a statin drug. In one embodiment, the pharmaceutical or nutraceutical composition does not comprise a statin drug.

In one embodiment, the method of improving cognitive function does not comprise the administration of a neuroprotective peptide. In one embodiment, the pharmaceutical or nutraceutical composition does not comprise a neuroprotective peptide. In one embodiment, the method of improving cognitive function does not comprise the administration of a peptide YY compound. In one embodiment, the pharmaceutical or nutraceutical composition does not comprise a peptide YY compound.

Synthesis of Cholesteryl Oleate or Analogues Thereof

In some embodiments, the cholesteryl oleate or analogues thereof may be purchased for use in accordance with the present invention. For example, cholesteryl oleate can be purchased from Sigma Aldrich (CAS 303-43-5), or other suppliers known to the person skilled in the art.

In other embodiments, cholesteryl oleate or analogues thereof may be synthesised by the reaction of cholesterol or analogues thereof with fatty acids, such as oleic acid. The fatty acid, such as oleic acid, may be prepared by methods known to the person skilled in the art either by chemical synthesis, extraction and purification from natural sources, or may be purchased from a supplier. The esterification described earlier to form cholesteryl oleate or analogues thereof is known to those skilled in the art.

EXAMPLES

Example 1—Sample Extraction

Sample Collection

Human brain tissue samples were obtained from the Victorian Brain Bank, and were isolated from a 25 year old healthy males, 75 year old healthy males, and 75 year old Alzheimer's disease patients.

Mice were anesthetised with isoflurane then given a non-recovery dose of lethabarb (pentobarbitone). While mice were unconscious, blood was collected via cardiac puncture. Blood was allowed clot on ice, then stored at −80° C. The brain was then removed from the skull, and the hippocampus and/or frontal cortex dissected and stored at −80° C.

Lipid Extraction

Dissected hippocampus or frontal cortex was weighed in cryomill tubes (10-30 mg). Whole blood was defrosted on ice and 50 µL was transferred to a new Eppendorf tube. 666 µL of 0.01% butylated hydroxytoluene in chilled methanol was added and only the brain samples were then homogenised in the cryomill (Preecellys®24) at the rotation speed of 6800 rpm for 30 seconds three times with cold maintainer (Cryolys®) at −17° C., maintained using liquid nitrogen. 333 µL of chloroform was added, then the tube was vortexed and shaken at room temperature for 30 mins. Samples were then centrifuged at 100 rpm at 0° C. for 10 mins. Supernatant was then transferred to a 2 ml Eppendorf tube. 1000 µL of 0.01% BHT in chilled methanol and chloroform (2:1) was added to pellet, then samples were vortexed, shaken and spun down again for extraction of protein precipitate. Supernatant from second extraction was combined with supernatant from the first extraction. Samples where then dried in vacuum dryer under nitrogen gas for complete dryness and stored at −20° C.

Liquid Chromatography/Mass Spectrometry (LC/MS) Analysis

Samples were resuspended in 100 µL of butanol/methanol (1:1) with 10 mM of ammonium formate. Samples were then shaken at 30° C. for 30 mins, then centrifuged at 100 rpm for 10 mins at room temperature. Supernatant was then transferred to LC analysis vials and analysed by Metabolomics Australia.

Lipids were separated by injecting 5 µL aliquots onto a 50 mm×2.1 mm×2.7 µm Ascentis Express RP Amide column (Supelco, Sigma, St Louis, USA) at 35° C. using an Agilent LC 1200 (Mulgrave, Australia), and eluted at 0.2 mLmin-1 over a 5 min gradient of water/methanol/tetrahydrofuran (50:20:30, v/v/v) to water/methanol/tetrahydrofuran (5:20:75, v/v/v), with the final buffer held for 3 min. Lipids were analysed by electrospray ionisation-mass spectrometry (ESI-MS) using an Agilent Triple Quad 6410 (Mulgrave, Australia). Lipid species from each lipid class were identified using precursor ion scanning from 100-1000 m/z, in positive ion mode, phosphatidylcholines (PC, precursors of m/z 184.1), sphingomyelins (SM, m/z 184.1), ceramides (CER, m/z 264.6), cholesterol esters (CE, m/z 369.4), phosphatidylglycerols (PG, m/z 189) and in negative ion mode phosphatidylinositols (PI, m/z 241). Neutral loss scanning was used to identify phosphatidylethanolamines (PE, in positive ion mode, neutral loss of m/z 141) and phosphatidylserines (PS, negative ion mode, m/z 87). Diacylglycerol (DAG) and Triacylglycerol (TAG) species were identified according to the neutral loss of fatty acyl moiety.

Identified lipid species were quantified using multiple reaction monitoring (MRM) with a 20 ms dwell time for the simultaneous measurements of ~20 to 50 compounds and the chromatographic peak width of 30 sec to 45 sec, a minimum data points collected across the peak was 12 to 16. Optimised parameters for capillary, fragmentor, and collision voltages were 4000 V, 140-380, and 15-60 V, respectively. In all cases, the collision gas was nitrogen at 7 Lmin$^{-1}$.

Lipid standards (Avanti Polar Lipids, Alabaster, USA) were prepared by combining equal volumes of individual lipid stock solutions. The standard solution was then diluted to provide a set of calibration solutions ranging in concentration from 0.1 to 10 µM. Calibration curves were constructed by least squares linear regression, fitting reverse phase peak area of the analyte against the concentration of the lipid in the reference standards. The concentration of each lipid species in the cell extract sample was estimated by using the regression model to convert normalized peak area to lipid concentration. Detected lipid species were annotated as follows; lipid class (sum of carbon atoms in the two fatty acid chains:sum of double bonds in the fatty acid chains). The LC/MS ESI-MRM data was processed using Agilent MassHunter quantitative software (version 6) (Mulgrave, Australia).

Example 2: Evaluation of Levels of Cholesteryl Oleate (CE 18:1), Cholesteryl Palmitate (CE 16:0) and Cholesteryl Palmitoleate (CE 16:1) in Human Frontal Cortex The levels of cholesteryl ester present in the frontal cortex of human subjects were determined. The human subjects ranged from 25 year old healthy males, 75 year old healthy males, and 75 year old Alzheimer's disease patients.

FIG. 1 outlines the range of cholesteryl esters present in the human frontal cortex, and FIG. 14 is a magnification of the cholesteryl esters in FIG. 1. Cholesteryl oleate (CE 18:1) is present in greater proportion compared to other fatty acid cholesterol esters. The levels of CE 18:1 are also represented in FIG. 2, which show that the levels of CE 18:1 in the white matter of control old subjects (75 year old males) is less than the levels of CE 18:1 in control young subjects (25 year old males), which indicates the levels of CE 18:1 decrease with ageing.

FIG. 2 also shows that the levels of CE 18:1 varies significantly with a subjects cognitive function, where the levels of CE 18:1 in the white matter of subjects suffering from Alzheimer's disease (AD) (75 year old AD patients) is statistically less than both the levels of CE 18:1 in the white matter of control young subjects (25 year old males) and control old subjects (75 year old males).

FIG. 3 shows that the levels of cholesteryl palmitate (CE 16:0) and cholesteryl palmitoleate (CE 16:1) also varies significantly with a subjects cognitive function, where the levels of CE 16:0 and CE 16:1 in the grey matter of subjects suffering from Alzheimer's disease (AD) (75 year old AD patients) is statistically higher than both the levels of CE 16:0 and CE 16:1 in the grey matter of control young subjects (25 year old males) and control old subjects (75 year old males).

Example 3: Evaluation of Levels of Cholesteryl Oleate in Mouse Brains

The levels of cholesteryl ester present in the mouse brains were determined in a 3 month old young mice. As seen in FIG. 4, the levels of cholesteryl oleate (CE 18:1) are significantly higher than the levels of other cholesteryl esters.

Example 4: Effect of Age on Levels of Cholesteryl Oleate in Mouse Frontal Cortex The effect of age on the levels of cholesteryl ester present in the mouse frontal cortex was determined, where the level of cholesteryl oleate (CE 18:1) in adult mice (7 months old) and aged mice (13 months and 21 months old) was evaluated. As seen in FIG. 5, the levels of CE 18:1 in the brain of aged mice (13 and 21 months old) is less than the levels of CE 18:1 in adult mice (7 months old), which indicates the levels of CE 18:1 decrease with ageing in mice (note that the average life span of mice is 2 years).

Example 5: Correlation Between Whole Blood CE 18:1 Levels and Brain Frontal Cortex CE 18:1 Levels in Mice The levels of CE 18:1 in whole blood compared to the levels of CE 18:1 in the brain frontal cortex from six 3 months old mice (young mice). The results are outlined in Table 1.

TABLE 1

Correlation between blood and brain frontal cortex CE (18:1) levels.

| Sample Name | Blood CE (18:1) | Brain FC CE (18:1) |
|---|---|---|
| Ar7 | 309577 | 2227.9 |
| K104 | 1077620 | 11195.5 |
| K106 | 308155 | 1373.6 |
| K139 | 1321716 | 14419.6 |
| K75 | 383841 | 1899.2 |
| K79 | 929401 | 11285.5 |
| O26 | 528763 | 5294.2 |

The correlation between whole blood CE 18:1 levels and brain frontal cortex CE 18:1 levels is outlined in FIG. 6, with an $R^2$ value of 0.976. Accordingly, determining the level of CE 18:1 in whole blood of a subject allows for the accurate determination of CE 18:1 levels in the brain frontal cortex of the same subject.

Example 6: Effect of Diet Containing Oleic Acid on Levels of Cholesteryl Oleate in Mice The effect of an oleic enriched diet on levels of cholesteryl oleate was evaluated. Old mice (19 to 21 months old) were fed either a control diet (no supplemented fatty acid or oil), 10% (w/w) palm oil (source of oleic acid) supplemented chow, or 10% (w/w) coconut oil (source of lauric acid) supplemented chow, over 6 weeks.

As seen in FIG. 7, a diet enriched in oleic acid resulted in a nearly two-fold increase in the levels of cholesteryl oleate compared to diets either absent of oleic acid (control), or enriched with other fatty acids (coconut oil).

Example 7: Cognitive Function Evaluation

The cognitive function of the mice was tested using a Barnes Maze. The Barnes maze makes use of a mouse's nature to avoid bright lights and open spaces. The Barnes maze was a white 150 cm disk with 36 evenly spaced holes. The disk is elevated 64 cm above the ground and four visual cues—two 3D cues and two 2D cues—are placed in four quadrants, denoting four possible escape holes. The escape box was placed under the assigned escape hole and fastened by tape. Four portable floodlights were used to evenly illuminate the maze and a light meter was used to ensure consistent brightness of 3400 to 3600 lux. Prior to the beginning of a trial, the maze and the escape box were cleaned with 80% ethanol to remove olfactory cues.

The mouse was placed in the centre of the maze under a cover. The cover was then retracted using a pulley system and the mouse was allowed to explore the maze for four minutes to find and enter the escape hole. If the mouse entered the escape hole in less than four minutes, the time was recorded and the floodlights switched off. If the mouse had not entered the escape hole after four minutes, the mouse was gently guided to the escape hole and lights were switched off. The mouse was allowed to remain in the escape box for one minute before it was returned to its home box outside the experimental room. For the probe trial, the escape box was removed and the trial length was shortened to 3 minutes (180 seconds). The duration required, distance traveled, and latency to the assigned escape hole was recorded using topscan lite 2.0. The time the mouse spent in the "target zone" (the 5 holes consisting of the assigned escape hole and the two holes on either side) searching for the assigned escape hole was also recorded.

Trials were conducted over seven days; day 1 contained a single habituation trial, days 2-6 contained 3 acquisition trials a day and day 7 contained a single probe trial.

Example 8: Effect of Oleic Acid Enriched Diet Compared to a Non-Fatty Acid Enriched Diet on Memory in Old Mice Old mice (19-21 months) were fed an oleic acid enriched diet comprising 10% (w/w) palm oil. Control old mice (21 months) were fed a non-oil supplemented control diet (no oleic acid). The cognitive function of the mice was tested using a Barnes Maze as described above.

The results are depicted in FIG. 8, where old mice (21 months) were fed an oleic acid enriched diet (10% palm oil), the old mice performed better in the Barnes maze than old mice fed on a control diet (no oleic acid), where the escape latency (seconds) the Barnes maze decreased significantly when the mice was fed oleic acid enriched diet, indicating increased cognitive function.

The time the mice spent searching for the escape hutch in the "target zone" during the probe trial is depicted in FIG. 10. Mice fed with an oleic acid enriched diet (10% palm oil) spent significantly more time searching for the escape hatch in the target zone (25 seconds, 13% of total time) than mice fed on a control diet with no oleic acid (12 seconds, 7% of total time), indicating increased cognitive function.

Example 9: Effect of Palm Oil and Coconut Oil Supplemented Diets on Memory in Old Mice Old mice (21 months) were fed a diet comprising 10% (w/w) palm oil (enriched with oleic acid). Control old mice (21 months) were fed a diet comprising 10% (w/w) coconut oil (enriched with other fatty acids but not enriched with oleic acid). The cognitive function of the mice was tested using a Barnes Maze as described above.

The results are depicted in FIG. 9, where old mice (21 months) were fed an oleic acid enriched 10% palm oil diet, the old mice performed better in the Barnes maze than old mice fed on a non-oleic acid enriched 10% coconut oil supplemented diet, where the escape latency (seconds) the Barnes maze decreased significantly when the mice was fed an oleic acid enriched oil supplemented diet compared with a non-oleic acid enriched oil supplemented diet, indicating increased cognitive function. The results show that an oleic acid enriched diet increases cognitive function compared to a diet of other oils that are enriched with different fatty acids, but not oleic acid.

Example 10: Effect of Cholesteryl Oleate (CE 18:1) Oral Administration on Memory in Old Mice The effect of a cholesteryl oleate oral administration on cognitive function was evaluated. In this study, the time mice spent at the target zone both before and after being fed a cholesteryl oleate (CE 18:1) enriched diet.

The CE 18:1 oral administration consisted of 20 mg CE 18:1 suspended in 0.5 g of raspberry flavoured agar jelly. To prepare the CE 18:1 enriched jelly, 4 g of agar powder and 0.1 g NaOH pellets was dissolved in 13 ml raspberry flavoured cordial, with MilliQ water added q.s. to form a total of 200 mL jelly solution. To the jelly solution, 400 mg of cholesteryl oleate was suspended in 40 ml of jelly to form the CE 18:1 oral administration.

Seven old mice (24 months old) were subjected to the Barnes Maze as described above, and the time the mice spent investigating the "target zone" during the probe trial was investigated. The same seven old mice were then fed 0.5 g of the CE 18:1 enriched jelly once a day (20 mg CE 18:1, 4% w/w), which correlated to a CE 18:1 dosage rate of 470 mg per kg of bodyweight. The mice were the subjected to the Barnes Maze as described above, and the time the mice spent investigating the "target zone" during the probe trial was investigated.

The time the mice spent investigating the "target zone" during the probe trials is outlined in Table 2.

TABLE 2

Effect of CE 18:1 oral administration on cognitive function.

| Mouse ID | Duration at target zone (s) | | Percentage of time spent at target zone out of 180 sec (%) | |
|---|---|---|---|---|
| | Before CE 18:1 | After CE 18:1 | Before CE 18:1 | After CE 18:1 |
| p9 | 2.76 | 21.28 | 1.53 | 11.82 |
| p11 | 4.64 | 9.04 | 2.58 | 5.02 |
| p7 | 4.28 | 16.00 | 2.38 | 8.89 |
| o72 | 17.52 | 16.48 | 9.73 | 9.16 |
| p6 | 21.64 | 28.68 | 12.02 | 15.93 |
| o78 | 0 | 4.84 | 0 | 2.69 |
| o76 | 8.44 | 23.40 | 4.69 | 13.00 |
| AVERAGE | 8.47 | 17.10 | 4.70 | 9.50 |

Before being fed with the CE 18:1 enriched diet, the mice spent an average of 8.47 seconds in the target zone (4.70% of the total probe trial time). After being fed with the CE 18:1 enriched diet, the same mice spent an average of 17.10 seconds in the target zone (9.5% of the total probe trial time). The data are also plotted in FIG. 11, which shows a statistical increase in time searching for the escape hatch in the target zone after being fed with the CE 18:1 enriched diet, indicating increased cognitive function.

Example 11: Levels of Cholesteryl Ester in Human Blood of Various Patient Types

The levels of cholesteryl ester present in blood of various human subjects were determined. The human subjects were either cognitive normal (CN), mild cognitive impaired (MCI) or Alzheimer's disease (AD) patients. The human subjects also either had beta-amyloid plaque detected in their brains (+) or had no beta-amyloid plaque detected in their brains (−). Briefly, beta-amyloid plaque has been shown to impact on cognitive function and may also be a precursor to Alzheimer's disease.

The levels of cholesteryl ester in the blood AD+, CN−, CN+, MCI−, and MCI+ patients is depicted in FIG. 12. The blood level of CE 18:1 in human patents with beta-amyloid plaque in the brain is lower than patients with no beta-amyloid plaque in the brain. Furthermore, the blood level of CE 18:1 in Alzheimer's disease patients (AD+) is statistically less than both cognitive normal patients and mild cognitive impaired patients both with or without the presence of beta-amyloid plaque in the brain (CN+, CN−, MCI+, and MCI−), highlighting that CE 18:1 can act as a biomarker for Alzheimer's disease.

Example 12: Levels of Cholesteryl Ester in Mice with Beta-Amyloid Plaque Deposits The levels of cholesteryl ester present in the whole brain of a AAP/PS1 transgenic 12 week-old female mouse (TgTg) compared with a wild type 12 week-old female mouse (WT) was determined. APP/PS1 are double transgenic mice expressing a chimeric mouse/human amyloid precursor protein (Mo/HuAPP695swe) and a mutant human presenilin 1 (PS1-dE9), both directed to CNS neurons. Both mutations are associated with early-onset Alzheimer's disease. These mice may be useful in studying neurological disorders of the brain, specifically Alzheimer's disease, amyloid plaque formation and aging.

The levels of cholesteryl ester in the brain of the TgTg and WT mice is depicted in FIG. 13. The amount of cholesteryl oleate (CE 18:1) in the TgTg mouse brain was significantly less than the amount of cholesteryl oleate in the WT mouse, indicating that the level of cholesteryl oleate decreases with the presence of beta-amyloid plaque in the brain.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from AU 2017904551 filed 9 Nov. 2017, the entire contents of which are incorporated herein by reference.

All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

The invention claimed is:

1. A method of improving cognitive function in a subject, the method comprising administering to the subject an effective amount of cholesteryl oleate, or an analogue thereof, wherein the cholesteryl oleate, or an analogue thereof, is selected from the group consisting of lanosteryl oleate, dihydrolanosteryl oleate, zymosteryl oleate, zymostenyl oleate, lathosteryl oleate, 7-dehydrodesmosteryl oleate, 8-dehydrocholesteryl oleate, 7-dehydrocholesteryl oleate, desmosteryl oleate and cholesteryl oleate, wherein the cholesteryl oleate, or an analogue thereof, is the only therapeutically active ingredient administered to the subject.

2. The method of claim 1, wherein the cholesteryl oleate, or an analogue thereof, is cholesteryl oleate.

3. The method according to claim 1, wherein the cholesteryl oleate, or an analogue thereof, is administered to the subject in an amount about 1 mg to about 1 g per kg of bodyweight of the subject.

4. The method according to claim 1, wherein the subject has been diagnosed with Alzheimer's disease or dementia.

\* \* \* \* \*